(12) United States Patent
Ye

(10) Patent No.: US 9,796,648 B2
(45) Date of Patent: Oct. 24, 2017

(54) GLYCEROL DEHYDRATION METHODS AND PRODUCTS THEREOF

(71) Applicant: University of Tennessee Research Foundation, Knoxville, TN (US)

(72) Inventor: Xiaofei Ye, Knoxville, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

(21) Appl. No.: 15/308,016

(22) PCT Filed: May 4, 2015

(86) PCT No.: PCT/US2015/029045
§ 371 (c)(1),
(2) Date: Oct. 31, 2016

(87) PCT Pub. No.: WO2015/168683
PCT Pub. Date: Nov. 5, 2015

(65) Prior Publication Data
US 2017/0057898 A1 Mar. 2, 2017

Related U.S. Application Data

(60) Provisional application No. 61/987,785, filed on May 2, 2014.

(51) Int. Cl.
| | |
|---|---|
| *C07C 45/52* | (2006.01) |
| *C07C 45/82* | (2006.01) |
| *C07C 51/00* | (2006.01) |
| *C07C 29/76* | (2006.01) |
| *C07C 51/235* | (2006.01) |
| *B01J 21/04* | (2006.01) |
| *B01J 21/06* | (2006.01) |
| *B01J 21/08* | (2006.01) |
| *B01J 23/30* | (2006.01) |
| *B01J 23/887* | (2006.01) |
| *B01J 29/40* | (2006.01) |
| *B01J 3/00* | (2006.01) |
| *B01J 3/04* | (2006.01) |
| *C07C 47/22* | (2006.01) |

(52) U.S. Cl.
CPC .............. *C07C 45/52* (2013.01); *B01J 3/008* (2013.01); *B01J 3/04* (2013.01); *B01J 21/04* (2013.01); *B01J 21/066* (2013.01); *B01J 21/08* (2013.01); *B01J 23/30* (2013.01); *B01J 23/8877* (2013.01); *B01J 29/40* (2013.01); *C07C 29/76* (2013.01); *C07C 45/82* (2013.01); *C07C 47/22* (2013.01); *C07C 51/235* (2013.01); *Y02P 20/584* (2015.11); *Y02P 20/588* (2015.11)

(58) Field of Classification Search
CPC ........ C07C 45/52; C07C 45/82; C07C 51/235
USPC .......................................... 568/486; 562/598
See application file for complete search history.

(56) References Cited

U.S. PATENT DOCUMENTS

| | | | |
|---|---|---|---|
| 4,035,417 A | 7/1977 | Izawa et al. | |
| 5,387,720 A * | 2/1995 | Neher | ..................... C07C 45/52 |
| | | | 568/449 |
| 5,907,075 A | 5/1999 | Subramaniam et al. | |
| 7,396,962 B1 * | 7/2008 | Dubois | ..................... C07C 45/52 |
| | | | 568/485 |
| 7,498,454 B2 | 3/2009 | Redlingshoefer et al. | |
| 7,655,818 B2 | 2/2010 | Dubois et al. | |
| 8,252,960 B2 | 8/2012 | Dubois et al. | |
| 9,447,011 B2 | 9/2016 | Ye et al. | |
| 2010/0204502 A1 | 8/2010 | Dubois | |
| 2011/0082319 A1 | 4/2011 | Dubois | |
| 2012/0231947 A1 | 9/2012 | Kerleau et al. | |
| 2012/0330049 A1 | 12/2012 | Paul et al. | |
| 2013/0053595 A1 | 2/2013 | Magatani et al. | |
| 2013/0303801 A1 | 11/2013 | Ueda et al. | |
| 2014/0081050 A1 * | 3/2014 | Subramaniam | ......... C07C 45/50 |
| | | | 568/454 |
| 2014/0114095 A1 * | 4/2014 | Kondo | ..................... C07C 29/76 |
| | | | 568/870 |

(Continued)

FOREIGN PATENT DOCUMENTS

| | | | |
|---|---|---|---|
| CN | 101225039 | * | 7/2008 |
| WO | WO 2010/076510 | | 7/2010 |
| WO | WO 2015/168683 | | 11/2015 |

OTHER PUBLICATIONS

Ai (1986) Selective Oxidation of Acrolein to Acrylic-Acid by V2O5—P2O5 Catalysts. Applied Catalysis, 27(1): 167-179.
Alhanash, et al. (2010) Gas-phase dehydration of glycerol to acrolein catalysed by caesium heteropoly salt. Applied Catalysis a-General, 378(1): 11-18.
Barrault, J., et al., Catalysis and fine chemistry. Catalysis Today, 2002. 75(1-4): 177-181.
Bertucco et al.( 1997) Catalytic hydrogenation in supercritical CO2: Kinetic measurements in a gradientless internal-recycle reactor. Industrial & Engineering Chemistry Research 36(7): 2626-2633.

(Continued)

*Primary Examiner* — Sikarl Witherspoon
(74) *Attorney, Agent, or Firm* — Jenkins, Wilson, Taylor & Hunt, P.A.

(57) ABSTRACT

Methods and systems for suppressing coking in dehydration reactions catalyzed by solid acids. Dehydration reactions catalyzed by one or more solid acid catalysts can be performed in the presence of a super critical carbon dioxide medium which prevents or minimizes coking of the solid acid catalysts. Methods and systems are provided for producing glycerol products, such as acrolein, acrylic acid, acetol, by performing a dehydration reaction of glycerol using one or more solid acid catalysts in the presence of a super critical carbon dioxide reaction medium. Such methods and systems can be nm for extended periods of time, or continuously, due to catalyst regeneration and/or recycling. Such methods and systems are configured to produce glycerol products from crude glycerol feedstock with minimal pretreatment.

24 Claims, 3 Drawing Sheets

(56) References Cited

U.S. PATENT DOCUMENTS

2014/0171676 A1 6/2014 Belliere-Baca et al.
2015/0299082 A1 10/2015 Ye et al.

OTHER PUBLICATIONS

Cavani al. (2010) The control of selectivity in gas-phase glycerol dehydration to acrolein catalysed by sulfated zirconia. Applied Catalysis B: Environmental 100(1): 197-204.
Chai et al.( 2009) Sustainable production of acrolein: Preparation and characterization of Zirconia-supported 12-tungstophosphoric acid catalyst for gas-phase dehydration of glycerol. Applied Catalysis a-General 353(2): 213-222.
Chai et al. (2007) Sustainable production of acrolein: investigation of solid acid-base catalysts for gas-phase dehydration of glycerol. Green Chemistry 9(10): 1130-1136.
Chapman et al. (2010) Continuous heterogeneous catalytic oxidation of primary and secondary alcohols in scCO(2). Green Chemistry 12(2): 310-315.
Chen et al. (2010) Biodiesel production from supercritical carbon dioxide extracted Jatropha oil using subcritical hydrolysis and supercritical methylation. Journal of Supercritical Fluids 52(2): 228-234.
Cheng et al. (2013) Acrolein Production from Crude Glycerol in Sub- and Super-Critical Water. Journal of the American Oil Chemists Society 90(4): 601-610.
Clark and Subramaniam (1998) Extended alkylate production activity during fixed-bed supercritical 1-butene/isobutane alkylation on solid acid catalysts using carbon dioxide as a diluent. Industrial & Engineering Chemistry Research 37(4): 1243-1250.
Conceicao et al.( 2012) Supercritical CO2 as an effective medium for a novel conversion of glycerol and alcohols in the heterogeneous telomerisation of butadiene. Green Chemistry 14(3): 673-681.
Corma et al. (2008) Biomass to chemicals: Catalytic conversion of glycerol/water mixtures into acrolein, reaction network. Journal of Catalysis 257(1): 163-171.
Ehlig-Economides & Economides (2010) Sequestering carbon dioxide in a closed underground volume. Journal of Petroleum Science and Engineering 70(1-2): 118-125.
Gläser & Weitkamp (2003) Supercritical carbon dioxide as a reaction medium for the zeolite-catalyzed alkylation of naphthalene. Industrial & engineering chemistry research 42(25): 6294-6302.
Gu et al. (2012) Study on the influence of channel structure properties in the dehydration of glycerol to acrolein over H-zeolite catalysts. Applied Catalysis a-General 429: 9-16.
Haider et al. (2012) Rubidium- and caesium-doped silicotungstic acid catalysts supported on alumina for the catalytic dehydration of glycerol to acrolein. Journal of Catalysis 286: 206-213.
Han & Poliakoff (2012) Continuous reactions in supercritical carbon dioxide: problems, solutions and possible ways forward. Chemical Society Reviews 41(4): 1428-1436.
Hsu et al.( 2010) Life cycle environmental impacts of selected US ethanol production and use pathways in 2022. Environmental science & technology 44(13): 5289-5297.
Hulteberg et al. (2013) Pore Condensation in Glycerol Dehydration. Topics in Catalysis 56(9-10): 813-821.
Hunter & Savage (2003) Acid-catalyzed reactions in carbon dioxide-enriched high-temperature liquid water. Industrial & engineering chemistry research 42(2): 290-294.
Jia et al. (2010) Small-sized HZSM-5 zeolite as highly active catalyst for gas phase dehydration of glycerol to acrolein. Journal of Catalysis 269(1): 71-79.
Katryniok et al. ( 2009) Towards the Sustainable Production of Acrolein by Glycerol Dehydration. Chemsuschem 2(8): 719-730.
Katryniok et al. (2010) Glycerol dehydration to acrolein in the context of new uses of glycerol. Green Chemistry 12(12): 2079-2098.
Katryniok et al. (2012) Regeneration of Silica-Supported Silicotungstic Acid as a Catalyst for the Dehydration of Glycerol. Chemsuschem 5(7): 1298-1306.
Katryniok et al. (2013) Recent Developments in the Field of Catalytic Dehydration of Glycerol to Acrolein. Acs Catalysis 3(8): 1819-1834.
Katryniok et al. (2010) A long-life catalyst for glycerol dehydration to acrolein. Green chemistry 12(11): 1922-1925.
Krisnandi et al. (2008) Glycerol Upgrading over Zeolites by Batch-Reactor Liquid-Phase Oligomerization: Heterogeneous versus Homogeneous Reaction. Chemsuschem 1(10): 835-844.
Lauriol-Garbay et al. (2011) New efficient and long-life catalyst for gas-phase glycerol dehydration to acrolein. Journal of catalysis 280(1): 68-76.
Lin (2001) Selective oxidation of propane to acrylic acid with molecular oxygen. Applied Catalysis a-General 207(1-2): 1-16.
Liu (2011) Roles of Non-thermal Plasma in Gas-phase Glycerol Dehydration Catalyzed by Supported Silicotungstic Acid. Ph.D. Dissertation. The University of Tennessee: Knoxville, pp. 1-224.
Liu et al. (2012) A Comparative Review of Petroleum-Based and Bio-Based Acrolein Production. Chemsuschem 5(7): 1162-1180.
Medina-Gonzalez et al. (2013) Phase equilibrium of the CO2/glycerol system: Experimental data by in situ FT-IR spectroscopy and thermodynamic modeling. Journal of Supercritical Fluids 73: 97-107.
Naraschewskiet al. (2011) On the Role of the Vanadium Distribution in MoVTeNbO(x) Mixed Oxides for the Selective Catalytic Oxidation of Propane. Topics in Catalysis 54(10-12): 639-649.
Notification Concerning Transmittal of International Preliminary Report on Patentability (Chapter I of the Patent Cooperation Treaty) corresponding to PCT/US2015/029045 dated Nov. 17, 2016.
Notification of Transmittal of the International Search Report and the Written Opinion of the International Searching Authority, of the Declaration corresponding to PCT/US2015/029045 dated Jul. 28, 2015.
Omata et al. (2013) Hydrothermal synthesis of W—Nb complex metal oxides and their application to catalytic dehydration of glycerol to acrolein. Catalysis Today 201: 7-11.
Possato et al.(2013) A comparative study of glycerol dehydration catalyzed by micro/mesoporous MFI zeolites. Journal of Catalysis 300: 102-112.
Rajaei et al. (2012) Investigation on the effect of different supercritical fluid extraction process on the activation of the R-134 catalyst. Journal of Supercritical Fluids 67: 1-6.
Santana & Akgerman (2001) Alkylation of isobutane with 1-butene on a solid acid catalyst in supercritical reaction media. Industrial & Engineering Chemistry Research 40(18): 3879-3882.
Shyu et al. (1997) Carbon dioxide water phase equilibria results from the Wong-Sandler combining rules. Fluid Phase Equilibria 130(1-2): 73-85.
Song (2006) Global challenges and strategies for control, conversion and utilization of CO2 for sustainable development involving energy, catalysis, adsorption and chemical processing. Catalysis Today 115(1-4): 2-32.
Stevens et al.( 2011) Could the energy cost of using supercritical fluids be mitigated by using CO2 from carbon capture and storage (CCS)? Green Chemistry 13(10): 2727-2733.
Subramaniam (2001) Enhancing the stability of porous catalysts with supercritical reaction media. Applied Catalysis a-General 212(1-2): 199-213.
Suprun et al.(2009) Acidic catalysts for the dehydration of glycerol: Activity and deactivation. Journal of Molecular Catalysis a-Chemical 309(1-2): 71-78.
Tao et al.(2013) Sustainable production of acrolein: catalytic performance of hydrated tantalum oxides for gas-phase dehydration of glycerol. Green Chemistry 15(3): 696-705.
Tichý & Machek (1992) Oxidation of acrolein on a multicomponent oxide catalyst. Catalysis letters 15(4): 401-404.
Tichy (1997) Oxidation of acrolein to acrylic acid over vanadium-molybdenum oxide catalysts. Applied Catalysis a-General 157(1-2): 363-385.
Tsukuda et al. (2007) Production of acrolein from glycerol over silica-supported heteropoly acids. Catalysis Communications 8(9): 1349-1353.

(56) References Cited

OTHER PUBLICATIONS

Vitry et. al.( 2003) Propane selective oxidation over monophasic Mo—V—Te—O catalysts prepared by hydrothermal synthesis. Topics in Catalysis 23(1-4): 47-53.

Vradman et al.( 2001) Regeneration of poisoned nickel catalyst by supercritical CO2 extraction. Industrial & Engineering Chemistry Research 40(7): 1589-1590.

Wang et al.( 2009) Catalytic dehydration of glycerol over vanadium phosphate oxides in the presence of molecular oxygen. Journal of Catalysis 268(2): 260-267.

Yamaguchi et al.(2008) Enhancement of glycerol conversion to acetol in high-temperature liquid water by high-pressure carbon dioxide. Chemistry Letters 37(9): 926-927.

Yong et al.( 2001) Refining of Crude Glycerine Recovered from Glycerol Residue by Simple Vacuum Distillation. Journal of Oil Palm Research 13(2): 39-44.

\* cited by examiner

GLYCEROL DEHYDRATION METHODS AND PRODUCTS THEREOF

RELATED APPLICATIONS

The presently disclosed subject matter claims the benefit of U.S. Provisional Patent Application Ser. No. 61/987,785, filed May 2, 2014; the disclosure of which is incorporated herein by reference in its entirety.

TECHNICAL FIELD

The presently disclosed subject matter relates in some embodiments to glycerol dehydration methods and products thereof. In some embodiments, the presently disclosed subject matter relates to methods and systems for producing glycerol products using supercritical and/or subcritical carbon dioxide (SCF $CO_2$) reaction medium.

BACKGROUND

The glycerol glut resulting from booming biodiesel industry has created an urgent need to quickly and effectively convert crude glycerol into value-added chemical products. This plays a role in the economic sustainability of integrated bio-refineries since the profitability of a renewable fuel production facility often relies on the value of its co-products. With glycerol's wide range of utility in specialty chemical production, biodiesel producers can find opportunity in the transformation of their byproduct stream. For example, there may be opportunities in synthesizing acrolein and acrylic acid from glycerol. Acrolein and acrylic acid find wide applications such as in water-soluble acrylate coating, textile treating agents, adhesives, thermosetting acrylic resin, and plastics. Polyacrylic acid and its copolymers have applications in the production of superabsorbent polymer, detergent intermediates, water/oil treatment polymers, dispersants, flocculants, packing materials, and thickeners.

Acrolein is commercially produced by controlled oxidation of propylene in gas phase, and it can be further partially oxidized into acrylic acid or used as a chemical synthesis intermediate for chemicals such as methionine (an essential amino acid mainly used in the formulation of animal feed), glutaraldehyde, and polyurethane. Unfortunately, the conventional method is heavily dependent on the fossil origin of propylene. Moreover, intensive efforts in recent years to convert glycerol to acrolein and acrylic acid has been hindered by rapidly deactivating catalysts due to coke accumulation on the surface of catalysts.

As such, improved methods and systems for conversion of glycerol to acrolein and other co-products are needed. More particularly, methods and systems for conversion of glycerol to acrolein and other co-products with increased efficiency are needed.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments methods for producing a glycerol product are provided, comprising exposing glycerol to a solid acid catalyst in a SCF $CO_2$ reaction medium, whereby a glycerol product is produced by solid acid catalyzed dehydration of the glycerol. In some embodiments, coking of the solid acid catalyst is decreased during the solid acid catalyzed dehydration of the glycerol in the presence of SCF $CO_2$ as compared to solid acid catalyzed dehydration of glycerol in the absence of an SCF $CO_2$ reaction medium. In some embodiments, the active lifetime of the catalyst is extended as compared to the active lifetime of the catalyst during glycerol dehydration in a reaction medium other than SCF $CO_2$. In some embodiments, the glycerol product is selected from the group consisting of acrolein, acrylic acid, acetol and combinations thereof. In some embodiments, the solid acid catalyst is selected from the group consisting of heteropoly acids, salts of heteropoly acids, zeolites, metal oxides, cation-exchange resins, carbonaceous solid acids, and combinations thereof.

In some embodiments, methods for producing a glycerol product further comprise using co-solvent of water along with the SCF $CO_2$. In some embodiments, the glycerol product comprises acrolein, wherein the method further comprises catalytic acrolein oxidation to acrylic acid, wherein the reaction medium for the catalytic acrolein oxidation comprises $CO_2$ or SCF $CO_2$. In some embodiments, the glycerol comprises crude glycerol. In some embodiments, the crude glycerol comprises about 1 wt. % to about 100 wt. % glycerol, 0 wt. % to about 70 wt. % soapstock, 0 wt. % to about 30 wt. % alcohol, and about 1 wt. % to about 95 wt. % water content.

In some embodiments, methods for producing a glycerol product further comprise a crude glycerol pretreatment step, comprising contacting the crude glycerol with activated charcoal, or contacting the crude glycerol with an ion-exchange resin, or a combination thereof. In some embodiments, the glycerol comprises about 0.025 wt. % to about 0.05% wt. % salt.

In some embodiments, methods for producing a glycerol product further comprise mixing SCF $CO_2$ and glycerol and exposing the mixture to a temperature range of about 200° C. to 400° C. and a pressure range of 3 MPa to 35 MPa in a dehydration reactor comprising the solid acid catalyst to thereby produce acrolein, and recovering the acrolein. In some embodiments, recovering the acrolein comprises fractional distillation. In some embodiments, SCF $CO_2$ comprises $CO_2$ having a critical temperature ($T_c$) greater than about 31.1° C. and a critical pressure ($P_c$) greater than about 7.38 MPa.

In some embodiments, methods for producing a glycerol product further comprise the use of two catalysts, wherein a first catalyst comprises a dehydration catalyst that catalyzes the dehydration of glycerol to acrolein and wherein a second catalyst comprises a partial oxidation catalyst that catalyzes the oxidation of acrolein to acrylic acid, acetic acid, propionic acid and/or combinations thereof.

In some embodiments, methods for producing a glycerol product further comprise recycling the catalyst, wherein recycling the active catalyst increases the active lifetime of the catalyst as compared to the active lifetime of the catalyst during glycerol dehydration in a reaction medium other than SCF $CO_2$.

In some embodiments, provided herein are compositions comprising a glycerol product produced by the disclosed methods and systems.

In some embodiments, provided herein are reaction systems for processing glycerol, comprising a conduit for transporting and mixing glycerol and reaction medium, a $CO_2$ source, a temperature and pressurization system for maintaining and controlling desired temperature and pressure, wherein the temperature and pressurization system comprises a heater and pressure pump sufficient to produce and maintain SCF $CO_2$, a dehydration reactor, and a distillation system, wherein the temperature and pressurization system, dehydration reactor and distillation system are operably connected to or associated with the conduit to provide for the processing of glycerol.

In some embodiments, the dehydration reactor comprises one or more solid acid catalysts. In some embodiments, the reaction system further comprises a source of pressurized oxygen or air. In some embodiments, the reactor is a merged bed reactor comprising a dehydration catalyst and a partial oxidation catalyst. In some embodiments, the reaction system is configured to be run continuously, wherein the reactor comprises a catalyst that is regenerated in the presence of SCF $CO_2$. In some embodiments, the dehydration reactor further comprises an apparatus for controlling the release of pressure and decrease of temperature.

In some embodiments, provided herein is a method of suppressing coking in dehydration reactions catalyzed by solid acids, comprising performing a dehydration reaction catalyzed by a solid acid catalyst in the presence of a SCF $CO_2$ medium, whereby coking of the solid acid catalyst is decreased when the reaction proceeds in the presence of the SCF $CO_2$ medium as compared to the same reaction in the absence of the SCF $CO_2$ medium. In some embodiments, a lifetime of the catalyst is increased as compared to the active lifetime of the catalyst during a dehydration reaction in a reaction medium that does not contain SCF $CO_2$.

Accordingly, it is an object of the presently disclosed subject matter to provide glycerol dehydration methods and products thereof. This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to embodiments set forth in the illustrations of the accompanying drawings. Although the illustrated embodiments are merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, but merely to clarify and exemplify the presently disclosed subject matter.

For a more complete understanding of the presently disclosed subject matter, reference is now made to the following drawings in which.

DETAILED DESCRIPTION

I. General Discussion

Figure 1:
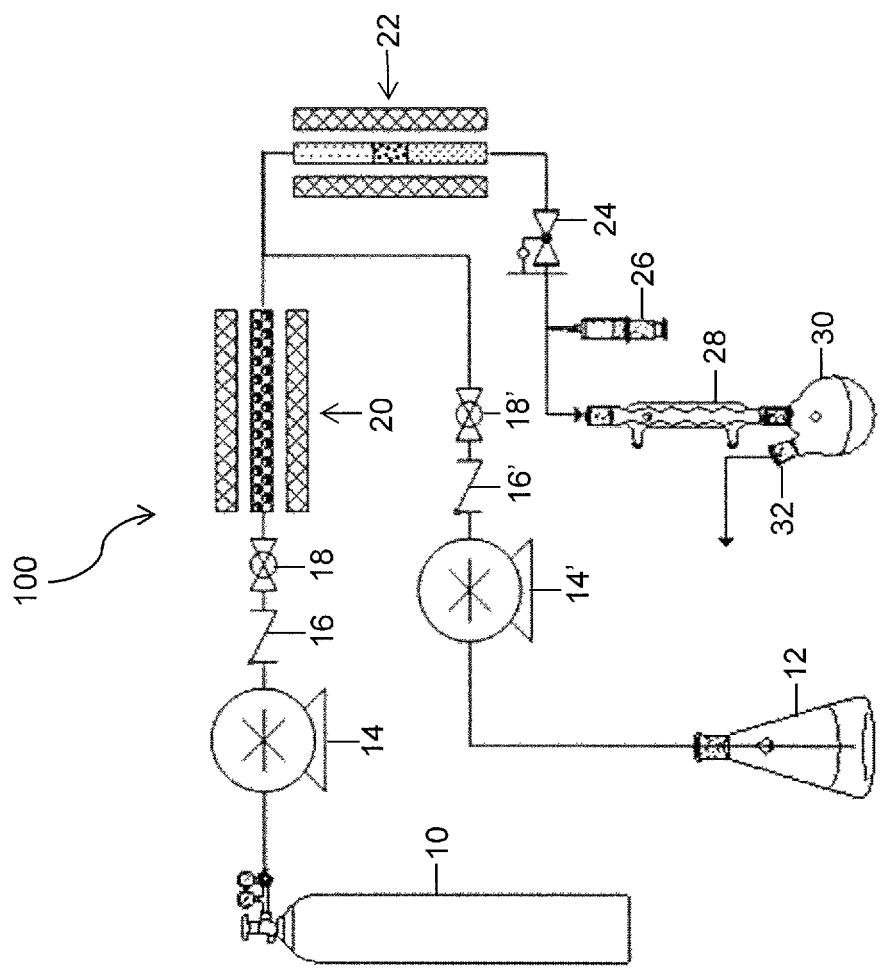
FIG. 1 is a schematic illustration of an embodiment of a glycerol dehydration system and method.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

Crude glycerol in nature is a complex mixture of glycerol, soapstock, free fatty acids, biodiesel residue, potassium or sodium salts (depending on different catalysts used in the biodiesel process), alcohol residue, and water. The concentration and level of glycerol and impurities can depend on the type of process and feedstocks that are used for biodiesel production. High-purity glycerol can be refined from crude glycerol, but often times at a high cost and significant energy consumption. Thus, methods and systems for converting glycerol, and particularly crude glycerol, to useful products are needed. Such methods and systems are disclosed herein.

Glycerol dehydration to acrolein is usually carried out between 250° C. and 320° C. either in gas or liquid phase catalyzed by acids. Generally, a gas-phase process with solid catalysts is preferred for glycerol dehydration to acrolein. Various solid acid catalysts can be used, including but not limited to supported heteropoly acids and their salts, zeolites and metal oxides. Unfortunately, these catalysts are not stable and deactivate very rapidly due to coke accumulation on the surface of catalysts. As a result, the active catalytic sites become less accessible and glycerol conversion can significantly decrease with increasing time-on-stream (TOS). For example, the glycerol conversion can drop significantly from about 90-100% efficiency to about 50-80% efficiency between 1 and 10 hours of TOS. This problem of coking and catalyst deactivation has become a key obstacle for the commercial production of acrolein and other products from glycerol. Previous attempts at solving the coking problem have been ineffective and/or impractical for industrial applications.

Disclosed herein are methods and systems for processing glycerol that in some embodiments use supercritical carbon dioxide and/or subcritical carbon dioxide, both of which can in some embodiments be referred to as SC $CO_2$ and/or supercritical fluid carbon dioxide (SCF $CO_2$), as a reaction medium to increase the efficiency of the processing by, at least in part, preserving and/or regenerating the catalyst or catalysts used in the processing. More particularly, in some embodiments methods and systems are provided for glycerol dehydration to acrolein where SCF $CO_2$ is used as a reaction medium to suppress and/or minimize coking on the catalyst to thereby extend the active lifetime of the catalyst. Such methods and systems overcome existing challenges with glycerol conversion to acrolein and other products, particularly with respect to coking and catalyst deactivation. Also provided herein is the use of SCF $CO_2$ to suppress and/or minimize coking on a catalyst in other dehydration reactions catalyzed by solid acids.

SCF $CO_2$ can in some embodiments comprise a $CO_2$ fluid beyond its critical temperature and/or critical pressure. For any fluid there is a unique critical temperature ($T_c$) and critical pressure ($P_c$). Thus, $CO_2$ fluid having temperature and pressure above its critical temperature and critical pressure is considered supercritical. Conversely, $CO_2$ fluid having either temperature or pressure below its critical temperature or critical pressure is considered subcritical. The given $T_c$ and $P_c$ uniquely define the critical state of $CO_2$ in a temperature (T)-pressure (P) phase diagram. The $T_c$ of $CO_2$ is 31.1° C. The $P_c$ of $CO_2$ is 7.38 MPa. Thus, in some aspects SCF $CO_2$, and particularly supercritical $CO_2$, comprises $CO_2$ fluid with a T greater than about 31.1° C., and a P greater than about 7.38 MPa. Conversely, in some aspects SCF $CO_2$, and particularly subcritical $CO_2$, comprises $CO_2$ fluid with a T less than about 31.1° C., and/or a P less than about 7.38 MPa. In some embodiments, SCF $CO_2$ can have a T from about 200-500° C. and a P from about 3-35 MPa. SCF $CO_2$ can comprise gas-like transport properties and liquid-like solvent power. In addition, SCF $CO_2$ is environmentally safe as it is non-toxic and non-flammable. SCF $CO_2$ can be obtained, for example, by carbon capture and storage (CCS).

In addition to providing methods and systems for dehydrating glycerol to acrolein, the instant disclosure in some embodiments also provides methods and systems for conversion of acrolein to additional products. For example, acrolein can be further partially oxidized to acrylic acid. In some embodiments, $CO_2$ from an upstream dehydration step (for conversion of glycerol to acrolein) can be used as a carrier gas and reaction medium for the partial oxidation of acrolein to acrylic acid (particularly at high space velocity). Based on the observation that over oxidation of acrolein can result in the production of $CO_2$, it was discovered that partial oxidation in $CO_2$ medium can help prevent over-oxidation of acrolein and increase selectivity to the desired product.

As such, disclosed herein are methods and systems to produce acrolein, acrylic acid, acetol and related products from glycerol using $CO_2$ and/or SCF $CO_2$ as reaction media that provide for extended activity and stability of catalysts, overcoming at least two major obstacles that are hindering the commercial production of acrolein and acrylic acid from glycerol: 1) fast deactivation of solid acid catalysts, and 2) the use of crude glycerol as feedstock. The disclosed methods and systems provide for 1) a continuous process directly using crude glycerol as feedstock with minimum pretreatment, 2) an environmentally safe process engineering using fixed-bed solid catalysts and environmentally safe reaction media, 3) a process for suppressing catalyst deactivation and facilitating product separation, 4) a process that can use a wide variety of solid acid catalysts, and 5) a process that can be scaled up and fitted into current chemical production facilities.

II. Definitions

Following long-standing patent law convention, the terms "a" and "an" mean "one or more" when used in this application, including the claims. Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter. Thus, the term "about", as used herein when referring to a value or to an amount of mass, weight, time, temperature, volume, or percentage is meant to encompass variations of ±20% or ±10%, more preferably ±5%, even more preferably ±1%, and still more preferably ±0.1% from the specified amount, as such variations are appropriate to perform the disclosed method.

The term "and/or" when used to describe two or more activities, conditions, or outcomes refers to situations wherein both of the listed conditions are included or wherein only one of the two listed conditions are included. The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim. As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole. As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

III. Methods and Systems for Producing Glycerol Products

Provided in some embodiments are methods and systems for producing a glycerol product comprising exposing glycerol to an acid catalyst, such as for example a solid acid catalyst, in a SCF $CO_2$ reaction medium, whereby a glycerol product is produced by solid acid catalyzed dehydration of the glycerol. By conducting the reaction in the presence of SCF $CO_2$ the frequency and/or degree of coking of the solid acid catalyst is decreased, diminished and/or minimized. Particularly, coking is decreased when the dehydration is conducted in the presence of SCF $CO_2$ as compared the absence of an SCF $CO_2$ reaction medium. By decreasing and/or minimizing coking of the catalysts the catalysts can be preserved, regenerated and/or recycled. Such preservation, regenerating and/or recycling of the active catalyst can in some embodiments significantly increase the active lifetime of the catalyst, particularly as compared to the active lifetime of the catalyst during glycerol dehydration in a reaction medium other than SCF $CO_2$. By way of example and not limitation, an increase in the active lifetime of the catalyst can increase the TOS in a method or system by as much as 10-fold, 20-fold, 50-fold or 100-fold, as compared to existing glycerol dehydration methods or systems. In some embodiments, a disclosed glycerol dehydration system or method can run for, or have a TOS of, about 100 hours, about 200 hours, about 300 hours, about 400 hours, about 500 hours, about 1,000 hours, about 2,000 hours or more, due to the regeneration of the catalyst. In some embodiments, a disclosed glycerol dehydration system or method can run continuously due to the regeneration of the catalyst.

The products produced from the conversion of glycerol using the disclosed methods and systems include but are not limited to acrolein, acrylic acid, acetol and combinations thereof. The solid acid catalyst used in the disclosed methods and systems include, but are not limited to, heteropoly acids, salts of heteropoly acids, zeolites, metal oxides, cation-exchange resins, carbonaceous solid acids, and combinations thereof. The solid acid catalysts disclosed and analyzed herein cover a wide range in acidity, surface area, and pore size, and demonstrate that the disclosed methods can be applied to a wide range of solid acid catalysts. The above-noted catalysts are exemplary only and not intended to be limiting of the instant disclosure.

In some aspects, the disclosed methods and systems can use a co-solvent of water along with the SCF $CO_2$ to enhance glycerol dehydration and minimize coking of the solid acid catalyst. In some aspects, by tuning the properties of the dehydration catalyst or catalysts (see Examples), another high-value co-product, acetol, can also be produced with significant yield, and acetol can be well separated.

The methods and systems disclosed herein can be configured to process crude glycerol, glycerol with minimal processing, and/or refined glycerol. Crude glycerol can be defined as, but not necessarily limited to, a glycerol product having about 1 wt. % to about 100 wt. % glycerol, 0 wt. % to about 70 wt. % soapstock, 0 wt. % to about 30 wt. % alcohol, and about 1 wt. % to about 95 wt. % water content. In some embodiments, crude glycerol can be processed, or minimally processed using a pretreatment method and/or system. In some embodiments, crude glycerol can be filtered with a column of packed activated charcoal, which can in part remove at least some organic-matter-non-glycerol. In some embodiments this can be followed by ion-exchange chromatography, such as for example using a chromatography system or column including an ion-exchange resin. Such a pretreatment method or system can result in a glycerol feedstock having about 0.025 wt. % concentration of salt. Such a salt concentration of this minimally refined or pretreated glycerol stock is about 10 times higher than that in commercial refined glycerol.

In some embodiments, the disclosed methods and systems for processing glycerol can comprise mixing SCF $CO_2$ and glycerol and exposing the mixture to a temperature range of about 200° C. to 400° C. and a pressure range of 3.5 MPa to 24 MPa in a dehydration reactor comprising the solid acid catalyst to thereby produce acrolein. Such a method can comprise recovering the acrolein by, for example, fractional distillation.

Still yet, in some aspects glycerol dehydration methods and systems can comprise the use of two catalysts, wherein a first catalyst comprises a dehydration catalyst that catalyzes the dehydration of glycerol to acrolein, and a second catalyst comprises a partial oxidation catalyst, including but not limited to mixed oxides, such as those based on Mo—V, Mo—Co, V—Sb, P—V and heteropolyacids that catalyzes the oxidation of acrolein to acrylic acid, acetic acid, propionic acid and/or combinations thereof. Alternatively, or in addition, such glycerol dehydration methods can comprise the production of acrolein from glycerol, and then a subsequent step of catalytic acrolein oxidation to acrylic acid. In such a configuration, the reaction medium for the catalytic acrolein oxidation can comprise $CO_2$ and/or SCF $CO_2$.

In some embodiments, reaction systems and configurations, as illustrated and discussed further herein, can comprise a conduit or tubing for transporting and/or mixing glycerol and a reaction medium. A $CO_2$ source can be provided in some configurations. Also, a temperature and pressurization system for maintaining and controlling desired temperature and pressure within the system can be provided. The temperature and pressurization system can in some aspects comprise a heater and pressure pump sufficient to produce and maintain SCF $CO_2$. Further, such a system can include a dehydration reactor configured to facilitate the dehydration of glycerol to acrolein and other products. The dehydration reactor can comprise one or more solid acid catalysts. In some aspects, a distillation system or other mechanism for recovering the glycerol product(s) can be provided as part of the system. In some embodiments, the temperature and pressurization system, dehydration reactor, and distillation system can be operably connected to or associated with the conduit to provide for the processing of glycerol throughout the system.

In some aspects a reaction system and/or configuration can further comprise a source of pressurized oxygen. Additionally, the system can comprise a reactor that is configured as a merged bed reactor comprising a dehydration catalyst as well as a partial oxidation catalyst, particularly where partial oxidation of acrolein to further products is desired.

With the benefit of reduced or minimized coking facilitated by SCF $CO_2$ reaction mediums, as disclosed and discussed further herein, some of the systems can be configured to be run continuously, or for extended periods of time, since the reduction or minimization in coking of the catalyst allows for the catalyst to be recycled and/or regenerated. This is in contrast to existing systems where coking can cause catalysts to decay and have a relatively short active lifespan. In such cases, the catalysts can require replacement and/or regeneration that necessitates discontinuation of the reaction process. Such is avoided in some embodiments of the disclosed reaction systems since the catalyst can be regenerated in the presence of SC $CO_2$ thereby facilitating continuous, or significantly extended, periods of operation.

Also provided herein in some embodiments are methods of suppressing coking in dehydration reactions catalyzed by solid acids. Such methods can comprise performing a dehydration reaction catalyzed by a solid acid catalyst in the presence of a SCF $CO_2$ medium. SCF $CO_2$ medium is compatible with a wide range of solid acid catalysts, including but not limited to supported heteropoly acids and their salts, zeolites, metal oxides, cation-exchange resins, and carbonaceous solid acids. As discovered and disclosed herein, conducting the dehydration reaction in the presence of a SCF $CO_2$ medium significantly decreases, minimizes and/or prevents coking of the solid acid catalyst. In some aspects, this decrease in coking is particularly noticeable when compared to the same reaction in the absence of the SCF $CO_2$ medium. In such methods the lifetime of the catalyst can be increased significantly as compared to the active lifetime of the catalyst during a dehydration reaction in a reaction medium that does not contain SCF $CO_2$. In some embodiments the increase in the lifetime of the catalyst is so significant that the TOS of a method or system using the catalyst is substantially increased, or made to run continuously, as discussed herein.

Methods and systems were engineered to facilitate glycerol conversion to useful products in an efficient and cost-effective manner. To test the methods and systems designed and disclosed herein, the process was divided into two steps: 1) using SCF $CO_2$ as reaction medium for the dehydration of glycerol to acrolein catalyzed by solid acids, and 2) using gaseous $CO_2$ as reaction medium for the partial oxidation of acrolein to acrylic acid catalyzed by mixed oxides. The two steps were then integrated into one continuous process converting glycerol to acrylic acid.

In some embodiments a glycerol dehydration method or system can comprise a configuration as depicted in FIG. 1. By way of example and not limitation, FIG. 1 depicts a schematic illustration of a glycerol dehydration system 100 that can comprise a $CO_2$ cylinder (or other supply of $CO_2$) 10, a glycerol solution 12, high pressure pumps 14 and 14', check valves 16 and 16', on-off valves 18 and 18', a $CO_2$ preheater 20, a reactor in tube furnace 22, a back pressure regulator 24, a gas sampling port 26, a condenser 28, a collection flask 30 and/or a vent 32. In such a configuration glycerol dehydration can be carried out in a reactor 22, such as a down-flow fixed-bed reactor made of a conduit or tubing material such as stainless steel tubing. Such a reactor 22 can in some embodiments be referred to as a fixed-bed reactor. In some embodiments a stainless steel tubing reactor can be approximately 300 mm to about 600 mm long with an inner diameter of about 5 mm to about 15 mm, an outer diameter of about 0.25 to about 0.75 inches, and a wall thickness of about 0.02 to about 0.1 inches. In some embodiments, such a down-flow fixed-bed reactor made of stainless steel tubing can be about 457.2 mm (18 inch) long with an about 9.4 mm inner diameter, and about 0.5 inch outer diameter, and a wall thickness of about 0.065 inches. The above dimensions and measurements can in some embodiments be suitable for a lab-scale system. In some embodiments, such a system can be scaled-up to industrially applicable dimensions.

In some embodiments, packing materials in tube reactor 22 can be held in place by a stainless steel frit. A solid acid catalyst diluted with silica sand or particles of silicon carbide can in some embodiments be packed in the middle of the tube, and silica sand can be filled in both the upper and lower ends.

When in use, and during each run of the glycerol dehydration method or system, liquid $CO_2$ from a cylinder 10 can be metered by a high pressure pump 14, such as a high pressure liquid $CO_2$ pump, through a preheater 20 (set at about 450° C. in some embodiments) and into reactor 22, up to a designated or predetermined pressure controlled by a back pressure regulator 24, and heated to a designated or predetermined temperature. Temperature at each of the $CO_2$ preheater 20 and reactor heater 22 can in some embodiments be independently controlled by a controller, such as for example a proportional-integral-derivative controller (PD controller). In some embodiments the predetermined pressure can be about 3 MPa to about 35 MPa. In some embodiments the predetermined temperature can be about 200° C. to about 500° C.

In some embodiments, glycerol solution 12 can be metered into reactor 22 by a high pressure pump 14', such as a high pressure syringe pump. In some embodiments, glycerol solution 12 can be about 5% w/v to about 100% w/v glycerol solution, in some embodiments about 10% w/v to about 30% w/v glycerol solution, and in some embodiments about 20% w/v glycerol solution. In some embodiments, glycerol solution 12 can be metered into reactor 22 when the pressure and reactor temperature become stable.

Glycerol from glycerol solution 12 can be dehydrated in the catalyst bed of reactor 22 to acrolein and other byproducts. After depressurization, the products can be cooled down and condensed in condenser 28 and collected in collection flask 30 for analysis. In some embodiments, a gas sampling syringe or port 26 can be used to sample the volatile organic products in $CO_2$ medium right after the back pressure regulator 24 for the analysis of acrolein, acetaldehyde, and propionaldehyde. Other major condensable byproducts and unconverted glycerol can in some aspects be analyzed by sampling the liquid in collection flask 30.

Figure 2:
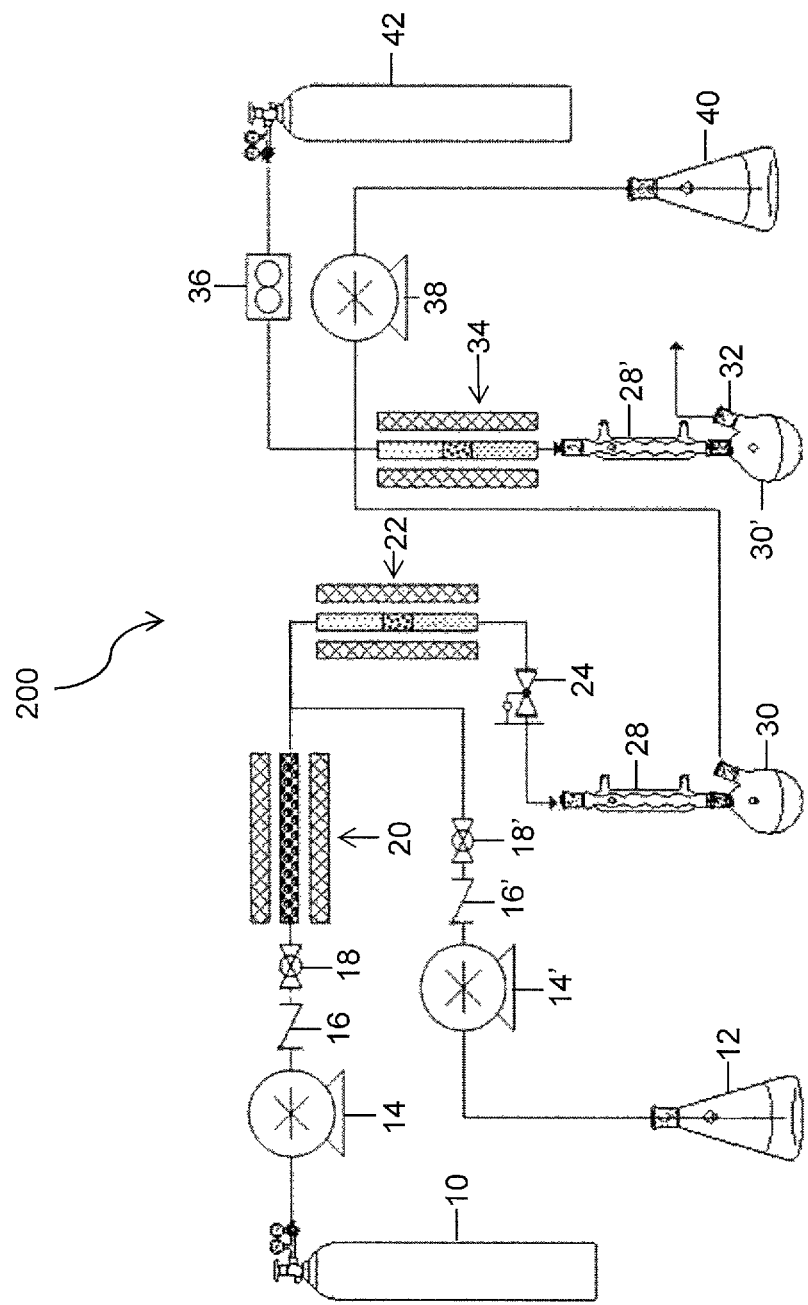
FIG. 2 is a schematic illustration of an embodiment of a glycerol dehydration system and method.

In some embodiments a glycerol dehydration method or system can comprise a configuration as depicted in FIG. 2. By way of example and not limitation, FIG. 2 depicts a schematic illustration of a glycerol dehydration system 200 that can comprise an integrated system or set-up including a $CO_2$ cylinder (or other supply of $CO_2$) 10, a supply of glycerol solution (e.g. glycerol and water) 12, high pressure pumps 14 and 14', check valves 16 and 16', on-off valves 18 and 18', a $CO_2$ preheater 20, a reactor in tube furnace (dehydration reactor) 22, a back pressure regulator 24, a condenser 28 or first stage condenser 28, a collection flask 30 or first collection flask 30, a partial oxidation reactor 34 or second reactor 34, a second stage condenser 28', a second collection flask 30', a vent 32, an oxygen or air mass flow controller 36, a water pump 38, a source of deionized (DI) water 40, and/or an oxygen cylinder 42.

In such a configuration as depicted in FIG. 2, glycerol dehydration can be carried out in an integrated dehydration-oxidation process. By way of example and not limitation, after the dehydration step as shown in FIG. 1, water and heavy products (e.g., unreacted glycerol, acetol, and removed coke precursors) can be condensed at a predetermined temperature, such as for example about 0° C. to about 100-200° C., in first condenser 28 and collected in first collection flask 30 for analysis. Uncondensed lighter products, mainly acrolein, acetaldehyde, and propionaldehyde, can be carried over by the depressurized $CO_2$ gas to the next step of partial oxidation. In some aspects, the temperature of first condenser 28 can be chosen at a temperature to completely condense all unreacted glycerol for analysis, e.g. about 0° C., or at a temperature suitable to maximize acrylic acid yield from glycerol.

In some aspects, partial oxidation of acrolein can be carried out in a down-flow fixed-bed reactor 22 made from stainless steel tubing, for example. Such a reactor 22 can comprise stainless steel tubing with a length of about 300 mm to about 600 mm, with an inner diameter of about 5 mm to about 15 mm, an outer diameter of about 0.25 to about 0.75 inches, and a wall thickness of about 0.02 to about 0.1 inches. In some embodiments, such a reactor 22 can comprise tubing of about 457.2 mm (18 inch) long by 10.922 mm inner diameter (outer diameter about 0.5 inches with a wall thickness of about 0.035 inches). The packing materials in the tube can be held in place by a stainless steel frit at the bottom. Silica sand or particles of silicon carbide can be filled first in the lower end, and catalyst can be packed in the middle of the tube, with quartz wool placed on top of the catalyst to serve as feed vaporization zone.

The temperature in reactor 22 can be at about 200° C. to about 400° C., in some embodiments about 300° C. Deionized water (DI water) can be pumped into the partial oxidation reactor 34 or second reactor 34 at about 1 mL/h to about 3 mL/h, or about 1.38 mL/h, to provide an acrolein: steam molar ratio of around 1:8.5. Oxygen, such as from oxygen cylinder 42, can be fed at about 4 mL/min to about 8 mL/min, or about 6 mL/min, controlled with a mass flow controller 36 to maintain an acrolein:oxygen ratio of approximately 1:1.5. Acrolein from the first dehydration step can be oxidized in the catalyst bed in second reactor 34 into acrylic acid and other byproducts (mainly acetic acid and propionic acid), which can be condensed and collected in the second collection flask 30'.

Figure 3:
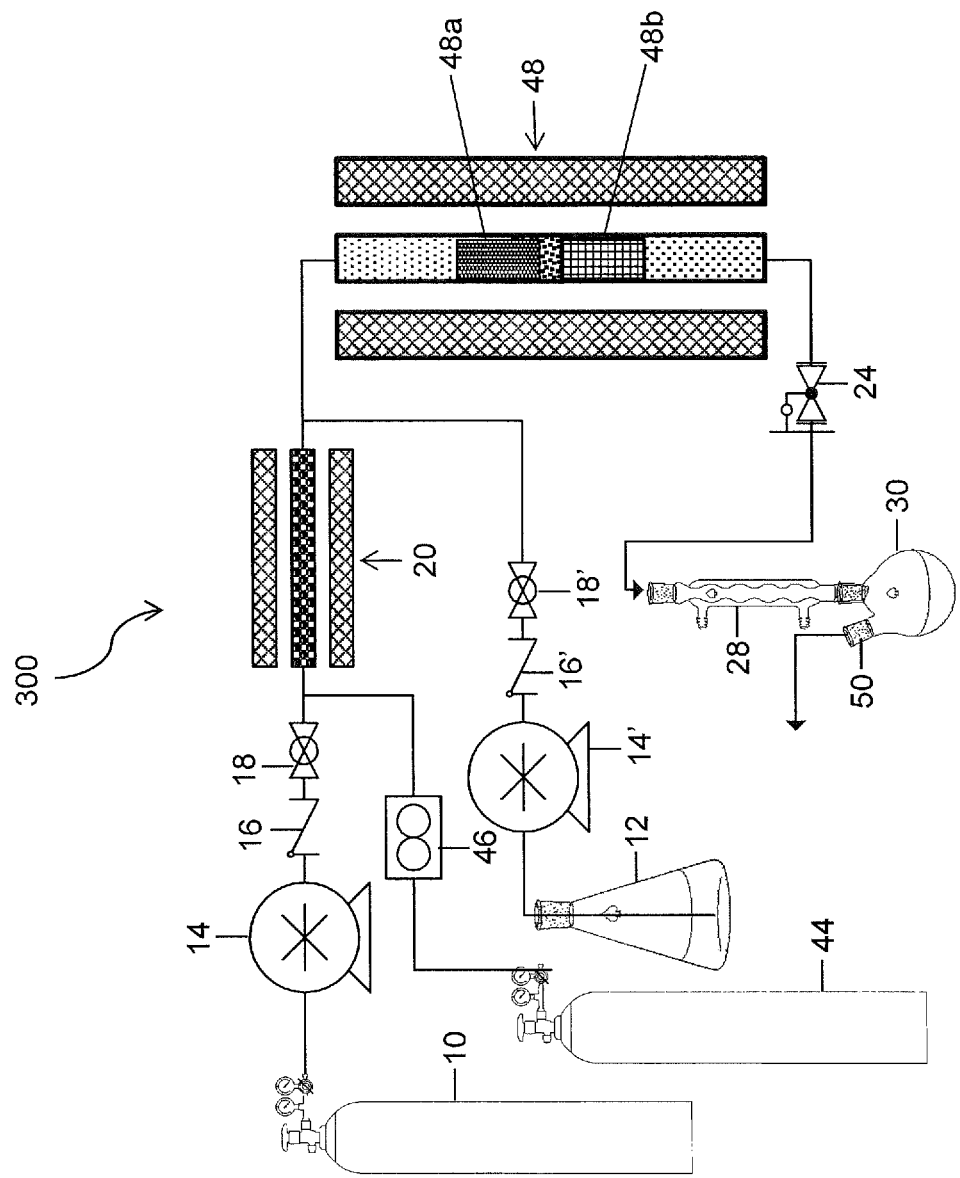
FIG. 3 is a schematic illustration of an embodiment of a glycerol dehydration system and method.

In some embodiments a glycerol dehydration method or system can comprise a configuration as depicted in FIG. 3. By way of example and not limitation, FIG. 3 depicts a schematic illustration of a glycerol dehydration system 300 can comprise a merged-bed one-step process including $CO_2$ cylinder (or other supply of $CO_2$) 10, a supply of glycerol solution (e.g. glycerol and water) 12, high pressure pumps 14 and 14', check valves 16 and 16', on-off valves 18 and 18', a $CO_2$ preheater 20, a supply of high pressure oxygen or air 44, a mass flow controller and valve 46, a merged-bed reactor for oxidehydration 48, a back pressure regulator 24, a condenser 28 for product condensation and separation, and a collection flask 30 for product collection.

In such a configuration as depicted in FIG. 3, glycerol dehydration can be carried out in a reaction system 300 comprising a merged-bed one-step process, as shown in FIG. 3. This is an alternative configuration to that depicted in FIG. 2 in that it merges the two reactors (22 and 34 in FIG. 2) into a single step using a single reactor 48 so that both the glycerol dehydration and partial oxidation of acrolein can be conducted in SCF $CO_2$. The merged bed can have separate packing of dehydration catalyst (48a) and partial oxidation catalyst (48b), or a multifunctional catalyst can be used. This configuration can in some embodiments render higher productivity by allowing the use of higher concentration glycerol feed 12 and speeding up reactions at oxidehydration conditions, while both catalysts can receive the benefit of decoking by SCF $CO_2$.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Materials Used in Methods

Standard chemicals for reaction and analysis, and precursors to make catalysts, including glycerol, acrolein, hydroxyacetone, acetaldehyde, propionaldehyde, acrylic acid, silicotungstic acid, hexaammonium heptamolybdate, ammonia metavanadate, copper (II) nitrate, iron (III) nitrate, tartaric acid and silica sand (99.8%), were purchased from Fisher Scientific (Pittsburgh, Pa., United States of America). Aluminum oxide and tungstated zirconia (15% $WO_3/ZrO_2$) were purchased from Alfa Aesar (Ward Hill, Mass., United States of America). Silica 1252 was provided by Grace Davison (Columbia, Md., United States of America). Zeolite powder of ZSM-5 (trade name CBV2314) in the ammonium form ($SiO_2/Al_2O_3$ molar ratio=23, surface area=425 $m^2/g$) was purchased from Zeolyst International (Conshohocken, Pa., United States of America). The physical properties of these catalysts or supports for the glycerol dehydration are summarized in Table 1.

TABLE 1

Physical properties of catalyst or catalyst support according to manufacturer's data

| Name | Si 1252 | $Al_2O_3$ | $WO_3/ZrO_2$ | ZSM-5 |
| --- | --- | --- | --- | --- |
| Shape | granules | Rings | pellets | powder |
| Particle size (mm) | 1-3 | 6.35 | 3 | N/A |
| Average pore diameter (nm) | 11 | 13 | 33.7 (medium) | 0.52 |

TABLE 1-continued

Physical properties of catalyst or catalyst support according to manufacturer's data

| Name | Si 1252 | $Al_2O_3$ | $WO_3/ZrO_2$ | ZSM-5 |
| --- | --- | --- | --- | --- |
| Pore volume (cc/g) | 1.02 | 0.77 | 0.28 | 0.25 |
| Surface area ($m^2/g$) | 390 | 150 | 118 | 425 |

Example 2

Catalyst Preparation-Dehydration Catalysts

Silicotungstic acid (HSiW) was loaded onto the catalyst supports ($Al_2O_3$ and $SiO_2$) by incipient impregnation. HSiW of 20% (wt. %) of the support was dissolved in deionized water and then added to the crushed/sieved support (particle size 250-400 μm) to make a slurry. After soaking for 24 hours, the resultant mixture was dried at 105° C. until complete dryness, and subsequently calcined at 350° C. in air for 3 hours. The two HSiW catalysts were denoted as HSiW/Si and HSiW/Al depending on the support used. $WO_3/ZrO_2$ was crushed and sieved into 250-400 μm and then calcinated at 400° C. in air for 3 hours before use. ZSM-5 zeolite was calcined to its active hydrogen form HZSM-5 at 550° C. in air for 5 hours; then the calcined zeolite powder was pressed at 20 MPa for 10 min, and crushed and sieved to 250-400 μm to be used.

The solid acid catalysts disclosed and analyzed above cover a wide range in acidity, surface area, and pore size, and were selected as examples to demonstrate that the disclosed methods can be applied to a wide range of solid acid catalysts. The above-noted catalysts are exemplary only and not intended to be limiting of the instant disclosure.

Example 3

Catalyst Preparation-Partial Oxidation Catalyst

Catalyst with the formula of $Mo_{12}V_3Cu_2Fe_{0.5}O_x$ was synthesized according to the procedures described in literature [48]. Briefly, solution A was prepared by mixing the aqueous solutions of hexaammonium heptamolybdate (24.7 g $(NH_4)_6Mo_7O_{24}.4H_2O$, 100 mL solution) and ammonia metavanadate (4.10 g $NH_4VO_3$, 300 mL solution); solution B was prepared by mixing the aqueous solutions of copper (II) nitrate (5.42 g $Cu(NO_3)_2.2.5H_2O$, 10 mL solution), iron(III) nitrate (2.36 g $Fe(NO_3)_3.9H_2O$, 10 mL solution), and tartaric acid (9.33 g $C_4H_6O_6$, 20 mL solution), among which tartaric acid was added as 40 wt. % of $MoO_3$ and $V_2O_5$ based on the results of Izawa et al. [47]. Solution A and B were mixed and the pH was adjusted to 7.6 by adding aqueous ammonia (27-30%). The clear blue-green solution was concentrated with constant stirring at 70° C. to obtain a paste which was then dried at 130° C. for 5 h, calcinated at 160° C. for 2 h and at 180° C. for 6 h, and finally annealed at 300° C. for 5 h and at 320° C. for 5 h. The calcined catalysts were pressed to form pellets at 20 MPa forces for 5 min. The pellets were then crushed and sieved to 400-841 μm to be used as catalyst. In some embodiments, the copper content of the partial oxidation catalyst was doubled, which resulted in improved performance in some embodiments. Such further formulation and/or optimization of these formulas can be performed without departing from the scope of the instant disclosure.

Example 4

Engineering of Catalytic Conversion of Glycerol

The process was divided into two steps to test the concepts of 1) using SCF $CO_2$ as reaction medium for the dehydration of glycerol to acrolein catalyzed by solid acids, and 2) using gaseous $CO_2$ as reaction medium for the partial oxidation of acrolein to acrylic acid catalyzed by mixed oxides. The two steps were then integrated into one continuous process converting glycerol to acrylic acid.

A schematic diagram of an exemplary experimental set-up for the dehydration step is shown in FIG. 1. Glycerol dehydration was carried out in a down-flow fixed-bed reactor made of 457.2 mm (18 inch) long by 9.4 mm inner diameter stainless steel tube (½ inch outer diameter with wall thickness of 0.065 inch). The packing materials in the tube reactor were held in place by a stainless steel frit. A solid acid catalyst diluted with silica sand or silicon carbide particles was packed in the middle of the tube, and silica sand or silicon carbide particles was filled in both the upper and lower ends. During each run, liquid $CO_2$ from a cylinder equipped with dip tube (Industrial grade, 99.8% purity, Airgas, Knoxville, Tenn., United States of America) was first metered by a high pressure liquid $CO_2$ pump (Model PU-1580, Jasco Analytical Instrument, Easton, Md., United States of America) through a preheater (set at 450° C.) into the reactor to a designated pressure controlled by a back pressure regulator and was heated up to a designed temperature. Temperature at each of the $CO_2$ preheater and reactor heater was independently controlled by a PID controller. When the pressure and reactor temperature became stable, 20% w/v glycerol solution was metered into the reactor by a high pressure syringe pump (model 500HV, Teledyne ISCO, Lincoln, Nebr., United States of America). Glycerol was dehydrated in the catalyst bed to acrolein and other byproducts. After depressurization, the products were cooled down and collected in a collection flask for analysis. Because of their high volatility, acrolein, acetaldehyde, and propionaldehyde can be difficult to be condensed completely under the high flow rate of $CO_2$ gas (~570 mL/min when the liquid $CO_2$ feeding rate was set at 1 mL/min). Therefore, a gas sampling syringe was used to sample the volatile organic products in $CO_2$ medium right after the back pressure regulator for the analysis of acrolein, acetaldehyde, and propionaldehyde. Other major condensable byproducts and unconverted glycerol were analyzed by sampling the liquid in the collection flask.

Conventional gas-phase glycerol dehydration to acrolein at atmospheric pressure using $CO_2$ as carrier gas was also conducted by modifying the reaction system shown in FIG. 1, including removing the back pressure regulator. The purpose was to compare it with glycerol dehydration in SCF $CO_2$ and to show that the use of SCF $CO_2$ significantly extends catalyst lifetime.

For the partial oxidation of acrolein to acrylic acid at high space velocity and atmospheric pressure, $N_2$ was first used as the carrier gas in order to find suitable reaction conditions. A conventional fixed-bed reaction system similar to that shown in FIG. 1 was also used by taking off the back pressure regulator. However, the space velocity used in this step was much higher than those reported in literature. The purpose was to find suitable reaction conditions (temperature, space velocity etc.) to be matched with the downstream of the first step reaction for integration.

A schematic diagram of an exemplary experimental set-up for the integrated dehydration-oxidation process is depicted in FIG. 2. After the dehydration step as shown in FIG. 1, water and heavy products (unreacted glycerol, acetol, and removed coke precursors) were condensed at 0° C. in the first condenser and collected in the first collection flask for analysis. Uncondensed lighter products, mainly acrolein, acetaldehyde, and propionaldehyde, were carried over by the depressurized $CO_2$ gas to the next step of partial oxidation. It is noteworthy to point out that about 5-10% of the acrolein produced was condensed in the first collection flask, reducing the possible acrylic acid yield in the next step. The first condenser temperature was chosen at 0° C. in order to completely condense all unreacted glycerol for analysis. Nonetheless, in some aspects the adjustment of the first condenser temperature remains as one parameter for optimizing the integrated system to maximize acrylic acid yield from glycerol.

Partial oxidation of acrolein was carried out in a down-flow fixed-bed reactor made of 457.2 mm (18 inch) long by 10.922 mm inner diameter stainless steel tube (outer diameter ½ inch with wall thickness 0.035 inch) at 300° C. (FIG. 2). The packing materials in the tube were held in place by a stainless steel frit at the bottom. Silica sand or silicon carbide particles were filled first in the lower end, and catalyst was packed in the middle of the tube, with quartz wool placed on top of the catalyst to serve as feed vaporization zone. During each run, deionized water (DI water) was pumped into the second reactor at 1.38 mL/h to provide an acrolein:steam molar ratio of around 1:8.5. Oxygen was fed at 6 mL/min controlled with a mass flow controller to maintain an acrolein:oxygen ratio of approximately 1:1.5. Acrolein from the first dehydration step was oxidized in the catalyst bed into acrylic and other byproducts (mainly acetic acid and propionic acid), which were condensed and collected in the second collection flask.

Gas and liquid samples were analyzed to evaluate the catalytic performance. They were quantified by injecting standard solutions with external calibration. Internal calibration was also periodically performed to ensure the accuracy. The condensed products in the collection flasks and volatile products sampled with a gas syringe were analyzed on a Agilent GC-FID 6890 (Santa Clara, Calif., United States of America) with a VB-WAX capillary column (0.25 mm ID, 30 m length, and 0.25 µm thickness of polyethylene glycol coating film) (Valco Instruments, Houston, Tex., United States of America). The following criteria were calculated to evaluate the catalytic performance.

$$\text{Glycerol conversion} = \frac{\text{Moles of loaded glycerol} - \text{Moles of unreacted glycerol}}{\text{Moles of loaded glycerol}} \times 100\%$$

$$\text{Product yield} = \frac{\text{Moles of carbon atoms in a product}}{\text{Moles of carbon atoms in loaded glycerol}} \times 100\%$$

$$\text{Product selectivity} = \frac{\text{Moles of carbon atoms in a product}}{\text{Moles of carbon atoms in reacted glycerol}} \times 100\%$$

$$\text{Carbon balance} = \frac{\text{Moles of carbon atoms in all measured compounds}}{\text{Moles of carbon atoms in loaded glycerol}} \times 100\%$$

Example 5

Results and Discussion

For the first step of glycerol dehydration in SCF $CO_2$, a series of 72-hour experimental runs was first conducted using different catalysts and reaction conditions listed in Table 2. The purpose was to compare the performance of different catalysts at different conditions in SCF $CO_2$ and with that in gaseous $CO_2$ for the first step of glycerol dehydration to acrolein.

TABLE 2

Catalysts and reaction conditions tested for glycerol dehydration to acrolein

| Entry[a] | Catalyst | Glycerol feed rate (mL/h) | Catalyst volume (mL) | Catalyst weight (g) | Temperature (° C.) | Pressure (MPa) |
|---|---|---|---|---|---|---|
| 1 | HSiW/Si | 6 | 3 | 1.4 | 275 | 8 |
| 2 | HSiW/Al | 6 | 3 | 1.7 | 275 | 8 |
| 3 | $WO_3/ZrO_2$ | 6 | 3 | 3.6 | 275 | 8 |
| 4 | $WO_3/ZrO_2$ | 6 | 3 | 3.6 | 275 | 16 |
| 5 | $WO_3/ZrO_2$ | 6 | 1 | 1.2 | 275 | 16 |
| 6 | $WO_3/ZrO_2$ | 6 | 1 | 1.2 | 275 | 24 |
| 7 | HZSM-5 | 6 | 3 | 1.8 | 275 | 8 |
| 8 | HZSM-5 | 6 | 3 | 1.8 | 300 | 8 |
| 9[b] | $WO_3/ZrO_2$ | 6 | 3 | 3.6 | 275 | 0.1 |

[a]All runs except for Entry 9 were conducted in SCF $CO_2$ with 1 mL/min liquid $CO_2$ flow rate using 20% w/v glycerol aqueous solution as feed.
[b]Entry 9 was conducted in gaseous $CO_2$ at atmospheric pressure with 60 mL/min gaseous $CO_2$ flow rate using 20% w/v glycerol aqueous solution as feed.

Example 6

Performance of Different Catalysts in SCF $CO_2$

The first step of glycerol dehydration in SCF $CO_2$ typically became stabilized after a couple of hours of TOS depending on the catalyst loading and reaction conditions. To fairly compare the performance of different catalysts, the average of glycerol conversion, and selectivity to acrolein and major byproducts for the first three hours TOS and TOS of 45-48 hours are summarized in Table 3; all of the four runs (corresponding to Entry 1, 2, 3 and 7 in Table 2) were conducted at the same condition: catalyst loading of 3.0 mL mixed with 5.0 mL of silica sand, reaction temperature of 275° C., 6 mL/h flow rate of 20% w/v glycerol feed, and 1 mL/min flow rate of liquid $CO_2$.

and −3.0 [10]. Stronger acidity above this range leads to a lower acrolein selectivity due to more severe coke deposition, while catalysts with a lower acidity was found to be not as effective for acrolein production. In addition, the pore size and channel structure of catalysts also influence the coke deposition.

As shown in Table 3 in 45-48 TOS, the highest glycerol conversion was 90.1% for $WO_3/ZrO_2$, which has a $H_0$ between −8.2 and −3.0 and an average mesopore diameter of 33.7 nm. Glycerol conversion decreased to 55.2% and 54.2% for HSiW/Si and HZSM-5, respectively, at 48 h TOS. This rapid decline of HSiW/Si activity could be attributed to its high acidity ($H_0$~−9) that resulted in serious coke deposition. HZSM-5 has very small pore openings of 0.51×0.55 nm, which is possibly the main reason for the quick decrease of activity. All catalysts showed high selectivity towards acrolein formation with HSiW/Si at the lower end at this experimental condition.

Besides acrolein, a number of side products were also detected, among which acetol was identified as the major one. In Table 3, high acetol yield was observed for $WO_3/ZrO_2$ (9.1%) and HZSM-5 (9.9%), indicating the higher number of Lewis acid sites in these two catalysts favoring acetol formation. Acetol (1-Hydroxyacetone) is also considered as a high-value chemical with wide industrial applications.

Furthermore, analysis of liquid products using Inductively Coupled Plasma-Atomic Emission Spectrometry (ICP-AES) according to EPA Method SW-846 6010B found no elements of Si, W, Zr, and Al present in the liquid products, indicating no leaching of the catalysts and the solid acids were stable under the reaction conditions and the SCF $CO_2$ media.

Example 7

Effect of SCF $CO_2$ Pressure

The effect of reaction pressure on glycerol dehydration in SCF $CO_2$ was investigated by comparing experimental Entries 5 and 6 in Table 2 using the same $WO_3/ZrO_2$ catalyst and reaction condition except for pressure. The catalyst

TABLE 3

Performance comparison in SCF $CO_2$ for the 4 dehydration catalysts[a]

| Entry | Catalyst | TOS (h) | Glycerol Conversion (%) | Product Selectivity (%) | | | | C Balance (%) |
|---|---|---|---|---|---|---|---|---|
| | | | | Acrolein | Acetol | Acetaldehyde | Propionaldehyde | |
| 1 | HSiW/Al | 0-3 | 100 | 70.2 | 2.1 | 2.5 | 4.2 | 78.9 |
| | | 45-48 | 73.9 | 85.6 | 7.2 | 2.4 | 4.2 | 99.6 |
| 2 | HSiW/Si | 0-3 | 100 | 59 | 2.9 | 0.9 | 1.8 | 64.6 |
| | | 45-48 | 55.2 | 50.2 | 6.9 | 0.8 | 0.9 | 77.3 |
| 3 | $WO_3/ZrO_2$ | 0-3 | 100 | 70.5 | 0 | 6.8 | 8.5 | 85.7 |
| | | 45-48 | 90.1 | 74.3 | 9.1 | 2.8 | 4.1 | 91.3 |
| 7 | HZSM-5 | 0-3 | 96.3 | 62.9 | 5.5 | 0.7 | 0.9 | 71.2 |
| | | 45-48 | 54.2 | 78.1 | 9.9 | 0.8 | 0.4 | 94.1 |

[a]All of the four runs (corresponding to Entry 1, 2, 3 and 7 in Table 2) were conducted at the same condition: catalyst loading of 3.0 mL mixed with 5.0 mL of silica sand, reaction temperature of 275° C., 6 mL/h flow rate of 20% w/v glycerol feed, and 1 mL/min flow rate of liquid $CO_2$.

Evidently, based on these results both the pore size and acidity of catalysts have influence on glycerol conversion and product selectivity. It was shown that the most effective acid strength range in Hammett acidity function ($H_0$) for selective acrolein production from glycerol is between −8.2 loading was reduced to 1 mL with intention to make the reaction reach stabilized stage faster.

Although phase diagram for this ternary system containing $CO_2$, water, and glycerol is complex and there are no literature data, observations disclosed herein show how the property change with pressure affect the catalytic performance. For example, when the pressure increases from 16 to 24 MPa, the density of SCF $CO_2$ increases from 162.8 to 245.2 kg/m$^3$, and the dielectric constant from 1.08 to 1.13. Water and glycerol might partially remain in liquid phase in this pressure range, and water properties show very slight change in the pressure range (density increases from 773.8 to 783.9 kg/m$^3$, dielectric constant increases from 24.2 to 24.7). Without being bound by any particular theory or mechanism of action, it is possible in some embodiments that the significant difference between the dielectric constant of SCF $CO_2$ and that of water indicates the existence of two phases of solvents in the system, and the SCF $CO_2$ with water as co-solvent could efficiently remove both hydrophobic and hydrophilic coke precursors before they polymerized into coke.

Glycerol dehydration in SCF $CO_2$ using $WO_3/ZrO_2$ was compared at 16 MPa and 24 MPa, with analysis of the effects on glycerol conversion and acrolein yield, and acrolein (ACR) and acetol (ACT) selectivity. Glycerol conversion at 16 MPa decreased quickly in 20 h TOS and then increased back slowly to around 60% at 72 h TOS, and it was always higher than that at 24 MPa. Without being bound by any particular theory or mechanism of action, this observation might in some embodiments indicate that the reactant glycerol existed in both liquid and gaseous phases, and higher pressure resulted in more liquid glycerol, reducing its conversion rate. The selectivity to acrolein remained stable around 70% with slight fluctuation after an initial 10 h induction period at 24 MPa. In addition, the acrolein selectivity at 24 MPa was always higher than that at 16 MPa, indicating that the selectivity is higher in the liquid phase but the glycerol conversion rate is higher in gaseous phase. Once the system reached equilibrium between coke precursor formation and removal on the outer surface of the catalysts, the gradual increase of glycerol conversion during 20-72 h TOS was observed, which can be explained by the long activation period of zirconia-based catalysts. This can be ascribed to the presence of Lewis acid sites [21, 24].

The initially rapid decline of glycerol conversion could in some aspects be at least partially due to that fact that not all catalytic sites were fully activated. Besides acting as a green solvent for decoking, $CO_2$ solubilized in water is also a weak Brønsted acid catalyst that has been used in many acid-catalyzed reactions [54, 55]. In addition, acrolein is mainly formed via the ionic pathway catalyzed by Brønsted acid sites [56]. The solubility of $CO_2$ in water is higher at 24 MPa than that at 16 MPa, and therefore this higher solubility gave rise to the increased ionic products and acrolein selectivity.

Example 8

Effect of Weight Hourly Space Velocity

The effect of Weight Hourly Space Velocity (WHSV) on glycerol dehydration in SCF $CO_2$ was investigated by comparing experimental Entry 4 vs. 5 as shown in Table 2. Glycerol conversion and acrolein yield, as well as ACR and ACT selectivity, were analyzed for glycerol dehydration in SCF $CO_2$ using $WO_3/ZrO_2$ at WHSV of 1 versus 0.33 h$^{-1}$. By increasing the catalyst loading from 1 mL to 3 mL while keeping other parameters constant, the WHSV decreased by three fold from 1 to 0.33 h$^{-1}$. At the same glycerol feed rate, larger amount of catalyst should have more active sites on the outer surface, and thus higher glycerol conversion should be achieved at steady state.

At WHSV=0.33 h$^{-1}$, glycerol conversion decreased from 100% to 79% in the initial 20 h of TOS, and then recovered gradually back to about 100%, probably due to slow activation of Lewis acid sites. Another possible explanation for this observation is that pore condensation occurred, and higher catalyst loading required longer time to reach an equilibrium for the adsorption (this also explains the dip at about 20 h TOS for the glycerol conversion curve at WHSV=0.33 h$^{-1}$).

As proposed, SCF $CO_2$ functions as a solvent removing coke precursors on the outer surface, and thus these active sites are enough to convert all glycerol at a lower WHSV (higher catalyst loading). More importantly, acrolein yield at WHSV=0.33 h$^{-1}$ only decreased slightly during the 72 h TOS, and always maintained at a high level, such as above 60%. At initial activation period within 30 h TOS, the selectivity to acrolein at WHSV=0.33 h$^{-1}$ was significantly higher than that at WHSV=1 h$^{-1}$, while the difference narrowed down in later TOS.

Example 9

Effect of Reaction Temperature

To investigate the effect of reaction temperature on catalytic performance in SCF $CO_2$, Entries 7 and 8 in Table 2 were compared. Glycerol conversion and acrolein yield, as well as ACR and ACT selectivity, were assessed for glycerol dehydration in SCF $CO_2$ using HZSM-5 at 275° C. and 300° C. HZSM-5 was used for this comparison and all the reaction conditions were the same except for reaction temperature.

The total reaction pressure was chosen at 8 MPa, which is slightly higher than the supercritical pressure of $CO_2$ ($P_c$=7.38 MPa) for the consideration of process economics. In addition, it was postulated that the temperature change would induce significant change in phase composition (liquid vs. gaseous) of water and glycerol, affecting glycerol conversion and product selectivity. However, no significant difference was observed for the product selectivity between the two tested temperatures. The constantly higher yield of acrolein at 300° C. was mainly due to the increased glycerol conversion, comparing with that at 275° C. This is in agreement with literature data showing that HZSM-5 needs a higher reaction temperature than $WO_3/ZrO_2$ or supported HSiW, and that glycerol conversion is higher at increased temperatures. Thus in SCF $CO_2$, 300° C. is suitable for HZSM-5 to achieve high glycerol conversion and acrolein yield.

Example 10

Comparison of Glycerol Dehydration in SCF $CO_2$ vs. Gas Phase $WO_3/ZrO_2$ catalyst was chosen for this comparison because Zr-based solid acids showed better stability and coking resistance with increasing TOS than HZSM-5 or supported HSiW in gas phase glycerol dehydration. Gas phase dehydration (Entry 9 in Table 2) was compared with Entry 4 at the same temperature and WHSV to justify the positive effects of SCF $CO_2$ in removing coke precursors and therefore extending catalyst lifetime. Glycerol conversion and acrolein yield, as well as ACR and ACT selectivity, were assessed for glycerol dehydration in SCF $CO_2$ versus gas phase using $WO_3/ZrO_2$ at 275° C.

Selectivity to both acrolein and acetol were lower in SCF $CO_2$ compared with that in gas phase. However, although glycerol conversion was complete in the initial 20 h TOS in gas phase reaction, it started to decline sharply thereafter, indicating quick deactivation that led to the significant reduction of acrolein yield. Acrolein yield decreased slightly from 73% to 62% in SCF $CO_2$ during the 72 h TOS, while it declined from 89% at 15 h TOS to only 34% at the end in gas phase. At the initial stage of gas phase reaction, the active sites on the catalysts are enough for the complete conversion of glycerol. However, once the coke started to build up, these active sites were continuously blocked and thus became unavailable. This comparison again indicates that SCF $CO_2$ is effective in extending catalyst lifetime in glycerol dehydration. While the reaction condition for gas phase as provided herein is in some embodiments at an optimal condition, glycerol dehydration in SCF $CO_2$ can in some embodiments be further optimized for both decoking and increasing acrolein yield without departing from the scope of the instant disclosure.

Example 11

Evidence of SCF $CO_2$ Removing Coke Precursor

Gas-chromatography mass-spectrometry (GC-MS) was used to assess the collected liquid samples. It was evident that the majority of acetaldehyde, propionaldehyde and acrolein were not condensed at the first stage condenser and passed down to the second stage of partial oxidation, while all acetol and unreacted glycerol were condensed and collected in the first collection flask. A significant amount of 1,4-dioxane-2,5-dimethanol and its isomers was detected in the first collection flask.

1,4-dioxane-2,5-dimethanol and its isomers are cyclic diglycerols. They are formed via acid-catalyzed dehydration reactions [59, 60]. These glycerol oligomers are considered as coke precursors as they can further polymerize into coke deposits blocking catalyst pore system [15, 17]. Table 4 shows the amount of cyclic diglycerols detected in liquid samples in the 9 experimental runs (refer to Table 2) during TOS 45-48 h.

TABLE 4

Yield of cyclic diglycerols in TOS 45-48 h

| Entry | Catalyst | Glycerol feed rate (mL/h) | Catalyst volume (mL) | Catalyst weight (g) | T (° C.) | P (MPa) | Diglycerol yield (mol %) |
|---|---|---|---|---|---|---|---|
| 1 | HSiW/Si | 6 | 3 | 1.4 | 275 | 8 | 5.3 |
| 2 | HSiW/Al | 6 | 3 | 1.7 | 275 | 8 | 4.9 |
| 3 | $WO_3/ZrO_2$ | 6 | 3 | 3.6 | 275 | 8 | 3.0 |
| 4 | $WO_3/ZrO_2$ | 6 | 3 | 3.6 | 275 | 16 | 3.2 |
| 5 | $WO_3/ZrO_2$ | 6 | 1 | 1.2 | 275 | 16 | 2.9 |
| 6 | $WO_3/ZrO_2$ | 6 | 1 | 1.2 | 275 | 24 | 2.8 |
| 7 | HZSM-5 | 6 | 3 | 1.8 | 275 | 8 | 3.7 |
| 8 | HZSM-5 | 6 | 3 | 1.8 | 300 | 8 | 2.8 |
| 9 | $WO_3/ZrO_2$ | 6 | 3 | 3.6 | 275 | 0.1 | 2.4 |

In a previous study on glycerol dehydration in gas phase catalyzed by supported HSiW [61], and a study on glycerol dehydration in sub- and super-critical water catalyzed by a homogeneous acid [56], cyclic diglycerols were sparsely detectable. However, in this study with the use of SCF $CO_2$, diglycerols yield of 5.3% and 4.9% were detected for silica and alumina supported HSiW, respectively (Entries 1 and 2). Since cyclic diglycerols are soluble in water, it is likely that they were eluted by water (at sub-critical conditions) and/or with the interaction with SCF $CO_2$. Also observed here were tar-like substances sticking to the walls of the first condenser and of the tube after the back pressure regulator that depressurized the SCF $CO_2$. These tar-like substances were eluted by SCF $CO_2$ because they were not soluble in water. GC-MS analysis of these tar-like substances showed that they mainly comprise complex ring-structured compounds including polycyclic aromatic hydrocarbons (coke or coke precursors). Therefore, without being bound by any particular theory or mechanism of action, it is possible that SCF $CO_2$ together with co-solvent of water enhanced the decoking performance by removing both polar and non-polar coke precursors from the solid acid catalysts. Although difficult to quantify the tar-like substances, a direct comparison shows that significantly less cyclic diglycerols (2.4%, Entry 9) in gas phase run were detected than those in SCF $CO_2$ with the same $WO_3/ZrO_2$ catalyst (3.2%, Entry 4). The extended catalyst lifetime for Entry 4 may be attributed to the removal of larger amount of diglycerols as coke precursor by the co-solvents of SCF $CO_2$ and water (see above for details).

Since the use of SCF $CO_2$ in glycerol dehydration is disclosed herein for the first time, further optimizations of the disclosed methods to improve decoking and further extend catalyst lifetime, and also to further increase acrolein yield, may be completed by one of ordinary skill in the art without departing from the scope of the instant disclosure. Such process parameters that could be optimized further to achieve such additional improvements can include but are not limited to reaction temperature, pressure and flow rate of SCF $CO_2$, ratio of co-solvents of SCF $CO_2$ and water, WHSV, and particle size of solid acid catalyst.

Example 12

Partial Oxidation of Acrolein to Acrylic Acid

The performance of the $Mo_{12}V_3Cu_2Fe_{0.5}O_x$ catalyst was first tested at regular space velocity and the results are shown in Table 5. No acrolein was detected in the condensate or the effluent gas. Therefore, the acrolein conversion reached 100% in all the runs.

TABLE 5

Partial oxidation of acrolein to acrylic acid at regular space velocity[a]

| Run | T (° C.) | $O_2$ flow rate (mL/min) | $N_2$ flow rate (mL/min) | AA Yield (%) |
|---|---|---|---|---|
| 1 | 250.0 | 6.0 | 51.0 | 69.7 |
| 2 | 250.0 | 4.5 | 51.0 | 64.4 |
| 3 | 240.0 | 4.5 | 51.0 | 37.5 |
| 4 | 260.0 | 4.5 | 51.0 | 61.8 |
| 5 | 270.0 | 4.5 | 51.0 | 63.3 |

[a]All runs were conducted at 0.056 mL/min feed rate of 15% w/v aqueous solution of acrolein with co-feeding DI water at 1.38 mL/h.

In some instances over-oxidation of acrolein can lower the yield of acrylic acid. As such, $O_2$ flow was reduced to 4.5 mL/min while other conditions remained unchanged (Run 2). However, the yield of acrylic acid slightly decreased. In Run 3, temperature was decreased to 240° C. with intention to weaken the effect of over-oxidation. Unfortunately, the yield of acrylic acid dropped drastically to only 37.5%, indicating that 250° C. seems to be the lowest temperature suitable to carry out acrolein partial oxidation in some embodiments. In Runs 4 and 5, temperature was increased, but a higher acrylic acid yield was not obtained.

To match the high $CO_2$ gas flow rate from the downstream of glycerol dehydration in SCF $CO_2$, the flow rate of $N_2$ was increased to investigate the performance of the catalyst at much higher space velocity, and the results are shown in Table 6.

TABLE 6

Partial oxidation of acrolein to acrylic acid at high space velocity[a]

| Run | T (° C.) | $O_2$ flow rate (mL/min) | $N_2$ flow rate (mL/min) | AA Yield (%) |
|---|---|---|---|---|
| 1 | 270.0 | 6.0 | 280.0 | 59.9 |
| 2 | 270.0 | 6.0 | 600.0 | 29.3 |
| 3 | 300.0 | 6.0 | 600.0 | 58.9 |
| 4 | 320.0 | 6.0 | 600.0 | 42.1 |

[a]All runs were conducted at 0.056 mL/min feed rate of 15% w/v aqueous solution of acrolein with co-feeding DI water at 1.38 mL/h.

The yield of acrylic acid decreased slightly to 59.9% when $N_2$ increased to 280 mL/min (Run 1), and further down to only 29.3% at $N_2$ flow of 600 mL/min in Run 2 (this is close to the flow rate of depressurized $CO_2$ from upstream). However, when the temperature was increased to 300° 0 (Run 3), the AA yield improved back to 58.9%. This indicates that the negative effect of high space velocity could be compensated by adjusting other reaction parameters, such as reaction temperature. When the temperature further increased to 320° C. in Run 4, AA yield reduced to 42.1%, implying that 300° C. may be the upper limit for this reaction at $N_2$ flow rate of 600 mL/min. In summary, a relatively high AA yield of 58.9% was obtained even at high space velocity, demonstrating the feasibility of connecting the glycerol dehydration in SCF $CO_2$ and the partial oxidation of acrolein at high gas space velocity. Therefore, it was decided to use the conditions of Run 3 for the integrated dehydration-oxidation process, although further optimization, particularly with respect to AA yield, can be performed without departing from the scope of the instant disclosure.

Example 13

Integrated Dehydration-oxidation Process

Based on the above tests on individual steps of glycerol dehydration and partial oxidation of acrolein, HZSM-5 was chosen as the dehydration catalyst for the integrated dehydration-oxidation process, since 1) it has the smallest pore size and pore volume that might contribute to its fast deactivation; and 2) it is an inexpensive solid acid commonly used in industry. Therefore, the worst-case scenario was tested and better decoking performance of SCF $CO_2$ in combination with other solid acids was expected. For the second step of partial oxidation of acrolein to acrylic acid, $Mo_{12}V_3Cu_2Fe_{0.5}O_x$ showed good stability after repeated uses, as long as the unconverted glycerol was condensed in the first condenser and did not enter the second step reaction (the catalyst can tolerate less than 5% of glycerol). The conditions for both steps was also adjusted. For the first step of glycerol dehydration in SCF $CO_2$, 3.075 g of HZSM-5 (about 5 mL, particle size 250-400 μm) diluted with 8.023 g silica sand (about 5 mL) was used as catalyst bed; the reaction was conducted at 320° C. and 8-8.3 MPa; and the feeding rate of 20% w/v aqueous glycerol solution was 6 mL/hr. For the second step of partial oxidation in gaseous $CO_2$, 10.6 g of $Mo_{12}V_3Cu_2Fe_{0.5}O_x$ (about 9 mL, particle size 400-841 μm) was used as catalyst bed; the reaction was conducted at atmospheric pressure and 300° C., and $O_2$ feeding rate was 6 mL/min with co-feeding of DI water at 1.38 mL/h. The results of a 528-hour TOS run using refined glycerol (99.5 wt. % purity) were assessed for carbon balance, glycerol conversion, and yield of acrolein and acrylic acid, as well as yield of acetol, acetic acid, acetaldehyde, propionaldehyde, propionic acid, and diglycerols.

Even after 528 hours TOS about 80% of glycerol conversion and about 30% of acrylic acid yield were still attained. Although gradual decreases of glycerol conversion and acrylic acid yield were observed, the rate of decrease was much smaller compared with results obtained with existing methods based on gas-phase reactions. The process could have kept going on even longer but it was terminated in these experiments because this 528-hour TOS is longer than any reported in literature, which was believed to be enough to show the novel concept of using SCF $CO_2$. Following this new concept of using $CO_2$ as reaction media, further improvement in catalysts and reaction conditions could lead to a continuous process for the production of acrolein/acrylic acid from glycerol viable for industrial applications.

The above experiment was repeated at the same conditions but using a different commercial zeolite catalyst with stronger acidity (Zeolite Y, CBV 500, Zeolyst International, Conshohocken, Pa., United States of America), which resulted in similar yield of acrolein and acrylic acid. However, the yield of acetol (about 17%) was much higher than that in the above experiment (about 10-12%), indicating another high-value co-product (acetol) can also be produced by tuning catalyst properties, and acetol is well separated/condensed in the first condenser. A series of long-time runs (>300 hours) using $WO_3/ZrO_2$ and another catalyst from the zeolite family, ZSM-22 (ACS Material, LLC, Medford, Mass., United States of America) in its hydrogen form, were also conducted, which illustrated that SCF $CO_2$ significantly prolonged the life-time of all these catalysts, although difference in products distribution was observed due to the different acidity and micro-structure of the catalysts.

Crude glycerol was then tested using identical conditions as above for refined glycerol. The crude glycerol acquired from industry had the following composition according to the manufacturer's specification: about 80% glycerol, about 15% water, less than 5% sodium chloride, and less than 1% methanol. Two simple pretreatment methods were used for the crude glycerol. The first one filtered the crude glycerol feed through a 1.5 μm glass microfiber filter to remove particulate contaminates, but did not remove the sodium salt. The second one distilled the crude glycerol at 250° C. under shop vacuum, and it was assumed that the salt was completely removed, although the distilled crude glycerol looked cloudier than refined glycerol. The purpose of this test was to examine how this method could handle crude glycerol to save cost at industrial scale, because the price of crude glycerol is significantly lower than that of refined glycerol.

In both cases using crude glycerol results similar to those using refined glycerol were achieved. However, gradual pressure drop across the dehydration catalyst bed was observed in both cases of crude glycerol, and the liquid $CO_2$ pump was automatically shut down when the pressure reached the set maximum of 10.5 MPa at about 42 h TOS. Observing the dehydration reactor after reaction revealed that the catalyst bed was clogged. In the case of filtered crude glycerol, the clogging occurred in the silica sand on top of the catalyst, likely due to the precipitation of sodium chloride at sub-critical water conditions, whereas it was clogged in the silica sand at the bottom of the catalyst in the case of distilled crude glycerol, probably due to reactions involving unspecified large molecules in the crude glycerol feed, such as residual oil, gums, free fatty acids, biodiesel, and polymerized compounds of glycerol formed in distillation.

Other than the clogging problem the reaction system appeared unaffected in handling the crude glycerol in terms of glycerol conversion and product yield. Detailed analysis of the clogging problem was then conducted. It was found that the impurities in crude glycerol affecting the glycerol conversion and catalyst life can be categorized as: 1) mainly salt, such as NaCl, and 2) a small amount of organic-matter-non-glycerol (OMNG), including residual oil, gums, free fatty acids, biodiesel (FAME), and polymerized compounds of glycerol. Current industrial glycerol purification mainly utilizes vacuum distillation, which is very costly due to the high boiling point of glycerol and the requisite intensive energy input. Notably, it was found that the catalyst was not "poisoned" by the salt, and the major problem was that the precipitated salt clogged the reactor. This clogging caused the change of reaction hydrodynamics, resulting in the decrease of glycerol conversion and eventual shut-down of reaction. In some embodiments it is expected that this potential clogging issue will be relieved at industrial scale-up.

Nevertheless, to establish that at lab scale crude glycerol with minimum pretreatment can be used for a long run, the following trials were conducted. First, the crude glycerol was filtered with a column of packed activated charcoal (the purpose was to remove the small amount of organic-matter-non-glycerol), followed by regular ion-exchange (ion-exchange resin IRN77 and IRN78 purchased from Sigma-Aldrich were used). This pretreatment resulted in a glycerol feed with about 0.025 wt. % concentration of salt. With this feedstock, a continuous run of 414 hours was achieved with similar product yields to those seen in the above examples, which was conducted at the identical reaction conditions using purified glycerol. Notably, no pressure drop was observed during the entire course. The salt concentration used was about 10 times higher than that in commercial refined glycerol.

Additionally, the ZSM-5 catalyst was modified through a mild desilication process that facilitated mass transfer into the catalyst pores. The commercial ZSM-5 catalyst was first soaked in 0.02 M of ammonium hydroxide at room temperature and pH 10.2 for 60 minutes with constant stirring, then the catalyst was collected via centrifugation, washed three times with DI water, dried in oven overnight, and calcined at 550° C. The calcinated zeolite powder was pressed at 20 MPa for 10 min, and crushed and sieved to 250-400 µm to be used. Repeating the experiment as described in the above paragraph resulted in similar product yields and distribution. However, the reaction appeared smoother, indicating the effect of the desilication process. This modification method remains as a viable way of improving catalyst performance in future development.

Example 14

Phase Diagram of the Ternary System and R&D Direction

Taking into account the impact of chemical processes on the environment, the search of innovative concepts for the substitution of volatile organic solvents in catalysis has become a tremendous challenge in academia and industry. In this context, SCF $CO_2$ and water provide advantages of environmentally friendly, or "green", reaction media. The experiments above demonstrate that the disclosed novel method works well for producing acrolein and acrylic acid and extending catalyst lifetime. The same technique may be applied in some embodiments to other processes where a bottleneck problem of catalyst deactivation in biomass conversion exists, such that other environmentally friendly processes are possible.

Studies showed that SCF $CO_2$ has very limited solubility in either water or glycerol in a binary system [63, 64]. However, no fundamental data concerning the ternary system of $CO_2$, water, and glycerol, as disclosed herein, is believed to be available. Better understanding of the three-phase (possibly, gas and liquid for $CO_2$, water, and glycerol, plus solid catalyst) system could in some aspects allow for further improvement of the disclosed process without departing from the scope of the instant disclosure.

Based on the experiments discussed above, and the disclosure herein, in some embodiments another configuration of reaction system can comprise a merged-bed one-step process, as shown in FIG. 3. This is an alternative configuration to that depicted in FIG. 2 in that it merges the two reactors into a single step so that both the glycerol dehydration and partial oxidation of acrolein can be conducted in SCF $CO_2$. The merged bed can have separate packing of dehydration catalyst (48a) and partial oxidation catalyst (48b), or a multifunctional catalyst can be used.

This configuration can in some embodiments render higher productivity by allowing the use of higher concentration glycerol feed and speeding up reactions at oxidehydration conditions, while both catalysts can receive the benefit of decoking by SCF $CO_2$.

Example 15

Crude Glycerol Pretreatment

The disclosed methods and systems are configured to process crude and/or refined glycerol. Nevertheless, to establish that at lab scale crude glycerol with minimum pretreatment can be used for a long run, the following trials were conducted. First, the crude glycerol was filtered with a column of packed activated charcoal, to remove the small amount of organic-matter-non-glycerol. This was followed by regular ion-exchange (ion-exchange resin IRN77 and IRN78 purchased from Sigma-Aldrich were used). This pretreatment resulted in a glycerol feed with about 0.025 wt. % concentration of salt. With this feedstock, a continuous run of 414 hours was achieved with similar product yields to those seen in the above examples, which was conducted at the same or similar reaction conditions using purified glycerol. Notably, no significant pressure drop was observed during the entire course. The salt concentration of the minimally refined or pretreated glycerol stock used was about 10 times higher than that in commercial refined glycerol.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

1. Liu, L., X. P. Ye, and J. J. Bozell, *A Comparative Review of Petroleum-Based and Bio-Based Acrolein Production.* Chemsuschem, 2012. 5(7): p. 1162-1180.
2. Katryniok, B., et al., *Glycerol dehydration to acrolein in the context of new uses of glycerol.* Green Chemistry, 2010. 12(12): p. 2079-2098.
3. Katryniok, B., S. Paul, and F. Dumeignil, *Recent Developments in the Field of Catalytic Dehydration of Glycerol to Acrolein.* Acs Catalysis, 2013. 3(8): p. 1819-1834.
4. Dubois, J.-L. M., Y. Y. Magatani, and K. Y. Okumura, *Process for manufacturing acrolein or acrylic acid from glycerin.* 2012, U.S. Pat. No. 8,252,960.
5. Tsukuda, E., et al., *Production of acrolein from glycerol over silica-supported heteropoly acids.* Catalysis Communications, 2007. 8(9): p. 1349-1353.
6. Chai, S. H., et al., *Sustainable production of acrolein: Preparation and characterization of Zirconia-supported 12-tungstophosphoric acid catalyst for gas-phase dehydration of glycerol.* Applied Catalysis a-General, 2009. 353(2): p. 213-222.
7. Magatani, Y., et al., *CATALYST AND PROCESS FOR PREPARING ACROLEIN AND/OR ACRYLIC ACID BY DEHYDRATION REACTION OF GLYCERIN.* 2013, US patent 20,130,053,595.
8. Jia, C. J., et al., *Small-sized HZSM-5 zeolite as highly active catalyst for gas phase dehydration of glycerol to acrolein.* Journal of Catalysis, 2010. 269(1): p. 71-79.
9. Possato, L. G., et al., *A comparative study of glycerol dehydration catalyzed by micro/mesoporous MFI zeolites.* Journal of Catalysis, 2013. 300: p. 102-112.
10. Chai, S. H., et al., *Sustainable production of acrolein: investigation of solid acid-base catalysts for gas-phase dehydration of glycerol.* Green Chemistry, 2007. 9(10): p. 1130-1136.
11. Omata, K., et al., *Hydrothermal synthesis of W—Nb complex metal oxides and their application to catalytic dehydration of glycerol to acrolein.* Catalysis Today, 2013. 201: p. 7-11.
12. Tao, L. Z., et al., *Sustainable production of acrolein: catalytic performance of hydrated tantalum oxides for gas-phase dehydration of glycerol.* Green Chemistry, 2013. 15(3): p. 696-705.
13. Dubois, J.-L., et al., *Process for dehydrating glycerol to acrolein.* 2010, U.S. Pat. No. 7,655,818.
14. Katryniok, B., et al., *Towards the Sustainable Production of Acrolein by Glycerol Dehydration.* Chemsuschem, 2009. 2(8): p. 719-730.
15. Suprun, W., et al., *Acidic catalysts for the dehydration of glycerol: Activity and deactivation.* Journal of Molecular Catalysis a-Chemical, 2009. 309(1-2): p. 71-78.
16. Corma, A., et al., *Biomass to chemicals: Catalytic conversion of glycerol/water mixtures into acrolein, reaction network.* Journal of Catalysis, 2008. 257(1): p. 163-171.
17. Hulteberg, C., A. Leveau, and J. G. M. Brandin, *Pore Condensation in Glycerol Dehydration.* Topics in Catalysis: p. 1-9.
18. Gu, Y. L., et al., *Study on the influence of channel structure properties in the dehydration of glycerol to acrolein over H-zeolite catalysts.* Applied Catalysis a-General, 2012. 429: p. 9-16.
19. Belliere-Baca, V., et al., *METHOD FOR PREPARING ACROLEIN FROM GLYCEROL OR GLYCERINE.* 2009, Google Patents.
20. Paul, S., et al., *METHOD FOR PREPARING ACROLEIN FROM GLYCEROL OR GLYCERINE.* 2012, U.S. Patent Publication US 2012/0330049.
21. Katryniok, B., et al., *Regeneration of Silica-Supported Silicotungstic Acid as a Catalyst for the Dehydration of Glycerol.* Chemsuschem, 2012. 5(7): p. 1298-1306.
22. Dubois, J.-L., C. Duquenne, and W. Holderich, *Process for dehydrating glycerol to acrolein.* 2008, U.S. Pat. No. 7,396,962.
23. Dubois, J.-L. M., *PROCESS FOR MANUFACTGURING ACROLEIN FROM GLYCEROL.* 2011: US.
24. Alhanash, A., E. F. Kozhevnikova, and I. V. Kozhevnikov, *Gas-phase dehydration of glycerol to acrolein catalysed by caesium heteropoly salt.* Applied Catalysis a-General, 2010. 378(1): p. 11-18.
25. Han, X. and M. Poliakoff, *Continuous reactions in supercritical carbon dioxide: problems, solutions and possible ways forward.* Chemical Society Reviews, 2012. 41(4): p. 1428-1436.
26. Bertucco, A., et al., *Catalytic hydrogenation in supercritical CO2: Kinetic measurements in a gradientless internal-recycle reactor.* Industrial & Engineering Chemistry Research, 1997. 36(7): p. 2626-2633.
27. Chen, C. H., et al., *Biodiesel production from supercritical carbon dioxide extracted Jatropha oil using subcritical hydrolysis and supercritical methylation.* Journal of Supercritical Fluids, 2010. 52(2): p. 228-234.
28. Chapman, A. O., et al., *Continuous heterogeneous catalytic oxidation of primary and secondary alcohols in scCO(2).* Green Chemistry, 2010. 12(2): p. 310-315.
29. Conceicao, L., R. Bogel-Lukasik, and E. Bogel-Lukasik, *Supercritical CO2 as an effective medium for a novel conversion of glycerol and alcohols in the heterogeneous telomerisation of butadiene.* Green Chemistry, 2012. 14(3): p. 673-681.
30. Song, C. S., *Global challenges and strategies for control, conversion and utilization of CO2 for sustainable development involving energy, catalysis, adsorption and chemical processing.* Catalysis Today, 2006. 115(1-4): p. 2-32.
31. Ehlig-Economides, C. and M. J. Economides, *Sequestering carbon dioxide in a closed underground volume.* Journal of Petroleum Science and Engineering, 2010. 70(1-2): p. 118-125.
32. Stevens, J. G., et al., *Could the energy cost of using supercritical fluids be mitigated by using CO2 from carbon capture and storage (CCS)?* Green Chemistry, 2011. 13(10): p. 2727-2733.
33. Hsu, D. D., et al., *Life cycle environmental impacts of selected US ethanol production and use pathways in 2022.* Environmental science & technology, 2010. 44(13): p. 5289-5297.
34. Subramaniam, B., *Enhancing the stability of porous catalysts with supercritical reaction media.* Applied Catalysis a-General, 2001. 212(1-2): p. 199-213.
35. Clark, M. C. and B. Subramaniam, *Extended alkylate production activity during fixed-bed supercritical 1-butene/isobutane alkylation on solid acid catalysts using carbon dioxide as a diluent.* Industrial & Engineering Chemistry Research, 1998. 37(4): p. 1243-1250.
36. Santana, G. M. and A. Akgerman, *Alkylation of isobutane with 1-butene on a solid acid catalyst in supercritical reaction media.* Industrial & Engineering Chemistry Research, 2001. 40(18): p. 3879-3882.
37. Gläser, R. and J. Weitkamp, *Supercritical carbon dioxide as a reaction medium for the zeolite-catalyzed alkylation*

37. *of naphthalene.* Industrial & engineering chemistry research, 2003. 42(25): p. 6294-6302.
38. Vradman, L., et al., *Regeneration of poisoned nickel catalyst by supercritical CO2 extraction.* Industrial & Engineering Chemistry Research, 2001. 40(7): p. 1589-1590.
39. Rajaei, H., et al., *Investigation on the effect of different supercritical fluid extraction process on the activation of the R-134 catalyst.* Journal of Supercritical Fluids, 2012. 67: p. 1-6.
40. Subramaniam, B. and M. C. Clark, *Solid acid supercritical alkylation reactions using carbon dioxide and/or other co-solvents.* 1999, Google Patents.
41. Kerleau, P., Dufresne, Pierre, *PROCESS FOR THE OFF SITE REGENERATION OF SOLID CATALYSTS.* 2012, US patent 20,120,231,947.
42. Naraschewski, F. N., A. Jentys, and J. A. Lercher, *On the Role of the Vanadium Distribution in MoVTeNbO(x) Mixed Oxides for the Selective Catalytic Oxidation of Propane.* Topics in Catalysis, 2011. 54(10-12): p. 639-649.
43. Vitry, D., et al., *Propane selective oxidation over monophasic Mo—V—Te—O catalysts prepared by hydrothermal synthesis.* Topics in Catalysis, 2003. 23(1-4): p. 47-53.
44. Lin, M. M., *Selective oxidation of propane to acrylic acid with molecular oxygen.* Applied Catalysis a-General, 2001. 207(1-2): p. 1-16.
45. Tichy, J., *Oxidation of acrolein to acrylic acid over vanadium-molybdenum oxide catalysts.* Applied Catalysis a-General, 1997. 157(1-2): p. 363-385.
46. Ai, M., *SELECTIVE OXIDATION OF ACROLEIN TO ACRYLIC-ACID BY V2O5-P2O5 CATALYSTS.* Applied Catalysis, 1986. 27(1): p. 167-179.
47. Izawa, S., et al., *Process for producing acrylic acid or methacrylic acid.* 1977, U.S. Pat. No. 4,035,417.
48. Tichý, J. and J. Machek, *Oxidation of acrolein on a multicomponent oxide catalyst.* Catalysis letters, 1992. 15(4): p. 401-404.
49. Haider, M. H., et al., *Rubidium-and caesium-doped silicotungstic acid catalysts supported on alumina for the catalytic dehydration of glycerol to acrolein.* Journal of Catalysis, 2012. 286: p. 206-213.
50. Katryniok, B., et al., *A long-life catalyst for glycerol dehydration to acrolein.* Green chemistry, 2010. 12(11): p. 1922-1925.
51. NIST, *NIST Reference Fluid Properties (version 9.1).* 2013.
52. Glaser, R. and J. Weitkamp, *Supercritical carbon dioxide as a reaction medium for the zeolite-catalyzed alkylation of naphthalene.* Industrial & Engineering Chemistry Research, 2003. 42(25): p. 6294-6302.
53. Lauriol-Garbay, P., et al., *New efficient and long-life catalyst for gas-phase glycerol dehydration to acrolein.* Journal of catalysis, 2011. 280(1): p. 68-76.
54. Hunter, S. E. and P. E. Savage, *Acid-catalyzed reactions in carbon dioxide-enriched high-temperature liquid water.* Industrial & engineering chemistry research, 2003. 42(2): p. 290-294.
55. Yamaguchi, A., et al., *Enhancement of glycerol conversion to acetol in high-temperature liquid water by high-pressure carbon dioxide.* Chemistry Letters, 2008. 37(9): p. 926-927.
56. Cheng, L. M., L. Liu, and X. P. Ye, *Acrolein Production from Crude Glycerol in Sub-and Super-Critical Water.* Journal of the American Oil Chemists Society, 2013. 90(4): p. 601-610.
57. Cavani, F., et al., *The control of selectivity in gas-phase glycerol dehydration to acrolein catalysed by sulfated zirconia.* Applied Catalysis B: Environmental, 2010. 100(1): p. 197-204.
58. Wang, F., J.-L. Dubois, and W. Ueda, *Catalytic dehydration of glycerol over vanadium phosphate oxides in the presence of molecular oxygen.* Journal of Catalysis, 2009. 268(2): p. 260-267.
59. Krisnandi, Y. K., et al., *Glycerol Upgrading over Zeolites by Batch-Reactor Liquid-Phase Oligomerization: Heterogeneous versus Homogeneous Reaction.* Chemsuschem, 2008. 1(10): p. 835-844.
60. Barrault, J., et al., *Catalysis and fine chemistry.* Catalysis Today, 2002. 75(1-4): p. 177-181.
61. Liu, L., Roles of Non-thermal Plasma in Gas-phase Glycerol Dehydration Catalyzed by Supported Silicotungstic Acid. 2011, Ph.D. Dissertation. The University of Tennessee: Knoxville.
62. YONG, K. C., et al., *REFINING OF CRUDE GLYCERINE RECOVERED FROM GLYCEROL RESIDUE BY SIMPLE VACUUM DISTILLATION.* Journal of Oil Palm Research, 2001. 13(2): p. 39-44.
63. Medina-Gonzalez, Y., et al., *Phase equilibrium of the CO2/glycerol system: Experimental data by in situ FT-IR spectroscopy and thermodynamic modeling.* Journal of Supercritical Fluids, 2013. 73: p. 97-107.
64. Shyu, G. S., et al., *Carbon dioxide water phase equilibria results from the Wong-Sandler combining rules.* Fluid Phase Equilibria, 1997. 130(1-2): p. 73-85.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for producing a glycerol product, comprising exposing glycerol to a solid acid catalyst in a supercritical or subcritical carbon dioxide (SCF $CO_2$) reaction medium, whereby a glycerol product is produced by solid acid catalyzed dehydration of the glycerol.

2. The method of claim 1, wherein coking of the solid acid catalyst is decreased during the solid acid catalyzed dehydration of the glycerol in the presence of SCF $CO_2$ as compared to solid acid catalyzed dehydration of glycerol in the absence of an SCF $CO_2$ reaction medium.

3. The method of claim 1, wherein the active lifetime of the catalyst is extended as compared to the active lifetime of the catalyst during glycerol dehydration in a reaction medium other than SCF $CO_2$.

4. The method of claim 1, wherein the glycerol product is selected from the group consisting of acrolein, acrylic acid, acetol and combinations thereof.

5. The method of claim 1, wherein the solid acid catalyst is selected from the group consisting of heteropoly acids, salts of heteropoly acids, zeolites, metal oxides, cation-exchange resins, carbonaceous solid acids, and combinations thereof.

6. The method of claim 1, further comprising using co-solvent of water along with the SCF $CO_2$.

7. The method of claim 1, wherein the glycerol product comprises acrolein, wherein the method further comprises catalytic acrolein oxidation to acrylic acid, wherein the reaction medium for the catalytic acrolein oxidation comprises $CO_2$ or SCF $CO_2$.

8. The method of claim 1, wherein the glycerol comprises crude glycerol.

9. The method of claim 8, wherein the crude glycerol comprises about 1 wt. % to about 100 wt. % glycerol, 0 wt. % to about 70 wt. % soapstock, 0 wt. % to about 30 wt. % alcohol, and about 1 wt. % to about 95 wt. % water content.

10. The method of claim 1, further comprising a crude glycerol pretreatment step, comprising:
contacting the crude glycerol with activated charcoal; or
contacting the crude glycerol with an ion-exchange resin; or
a combination thereof.

11. The method of claim 10, wherein the glycerol comprises about 0.025 wt. % to about 0.05% wt. % salt.

12. The method of claim 1, further comprising:
mixing SCF $CO_2$ and glycerol and exposing the mixture to a temperature range of about 200° C. to 400° C. and a pressure range of 3 MPa to 35 MPa in a dehydration reactor comprising the solid acid catalyst to thereby produce acrolein; and
recovering the acrolein.

13. The method of claim 12, wherein recovering the acrolein comprises fractional distillation.

14. The method of claim 1, wherein SCF $CO_2$ comprises $CO_2$ having a critical temperature ($T_c$) greater than about 31.1° C. and a critical pressure ($P_c$) greater than about 7.38 MPa.

15. The method of claim 1, further comprising the use of two catalysts, wherein a first catalyst comprises a dehydration catalyst that catalyzes the dehydration of glycerol to acrolein and wherein a second catalyst comprises a partial oxidation catalyst that catalyzes the oxidation of acrolein to acrylic acid, acetic acid, propionic acid and/or combinations thereof.

16. The method of claim 1, further comprising recycling the catalyst, wherein recycling the active catalyst increases the active lifetime of the catalyst as compared to the active lifetime of the catalyst during glycerol dehydration in a reaction medium other than SCF $CO_2$.

17. A reaction system for processing glycerol, comprising:
a conduit for transporting and mixing glycerol and reaction medium;
a $CO_2$ source;
a temperature and pressurization system for maintaining and controlling desired temperature and pressure, wherein the temperature and pressurization system comprises a heater and pressure pump sufficient to produce and maintain SCF $CO_2$;
a dehydration reactor; and
a distillation system,
wherein the temperature and pressurization system, dehydration reactor and distillation system are operably connected to or associated with the conduit to provide for the processing of glycerol.

18. The reaction system of claim 17, wherein the dehydration reactor comprises one or more solid acid catalysts.

19. The reaction system of claim 17, further comprising a source of pressurized oxygen or air.

20. The reaction system of claim 17, wherein the reactor is a merged bed reactor comprising a dehydration catalyst and a partial oxidation catalyst.

21. The reaction system of claim 17, wherein the reaction system is configured to be run continuously and wherein the reactor comprises a catalyst that is regenerated in the presence of SCF $CO_2$.

22. The system of claim 17, further comprising an apparatus for controlling the release of pressure and decrease of temperature.

23. A method of suppressing coking in dehydration reactions catalyzed by solid acids, comprising performing a dehydration reaction catalyzed by a solid acid catalyst in the presence of a SCF $CO_2$ medium, whereby coking of the solid acid catalyst is decreased when the reaction proceeds in the presence of the SCF $CO_2$ medium as compared to the same reaction in the absence of the SCF $CO_2$ medium.

24. The method of claim 22, wherein a lifetime of the catalyst is increased as compared to the active lifetime of the catalyst during a dehydration reaction in a reaction medium that does not contain SCF $CO_2$.

\* \* \* \* \*